United States Patent [19]

Milner

[11] Patent Number: 6,077,836
[45] Date of Patent: Jun. 20, 2000

[54] PERITONEAL DIALYSIS AND COMPOSITIONS FOR USE THEREIN

[75] Inventor: Jeremiah Milner, Roscrea, Ireland

[73] Assignee: ML Laboratotries, PLC, United Kingdom

[21] Appl. No.: 07/988,023

[22] Filed: Dec. 9, 1992

Related U.S. Application Data

[63] Continuation of application No. 07/335,750, Apr. 10, 1989, abandoned, which is a continuation-in-part of application No. 07/157,720, Feb. 19, 1988, abandoned, which is a division of application No. 06/891,342, Jul. 31, 1986, abandoned, which is a continuation-in-part of application No. 06/699,088, Feb. 7, 1985, abandoned, which is a continuation-in-part of application No. 06/569,760, Jan. 10, 1984, abandoned.

[30] Foreign Application Priority Data

Jan. 12, 1983 [GB] United Kingdom ............... 8300718
Feb. 18, 1984 [GB] United Kingdom ............... 8404299

[51] Int. Cl.$^7$ .................................... A61K 31/70
[52] U.S. Cl. .............................. 514/54; 514/60
[58] Field of Search ....................... 514/54, 60

[56] References Cited

U.S. PATENT DOCUMENTS

| 3,663,369 | 5/1972 | Morehouse et al. ............ 514/54 |
| 4,322,407 | 3/1982 | Ko ..................................... 514/54 |
| 4,761,237 | 8/1988 | Alexander et al. ............. 210/647 |

FOREIGN PATENT DOCUMENTS

| 8203329 | 10/1982 | WIPO ............................ 514/54 |
| 8300087 | 1/1983 | WIPO ............................ 514/54 |

*Primary Examiner*—Elli Peselev
*Attorney, Agent, or Firm*—William E. O'Brien; Stuart D. Frenkel

[57] ABSTRACT

A peritoneal dialysis composition containing an osmotic agent comprising a glucose polymer mixture, said mixture including at least 15% by weight of glucose polymers having a D.P. (degree of polymerization) greater than 12. A method is provided for preparing the glucose polymers and a defined sterile aqueous solution of the same for use in peritoneal dialysis by introduction into the abdominal cavity. Also disclosed are methods of treating toxaemia caused by toxins arising from internal disorders of the body, such as hepatic encephalopathy, or which arise from external sources such as poisoning by overdoses of drugs or industrial and agricultural chemicals, e.g., paraquat.

22 Claims, 7 Drawing Sheets

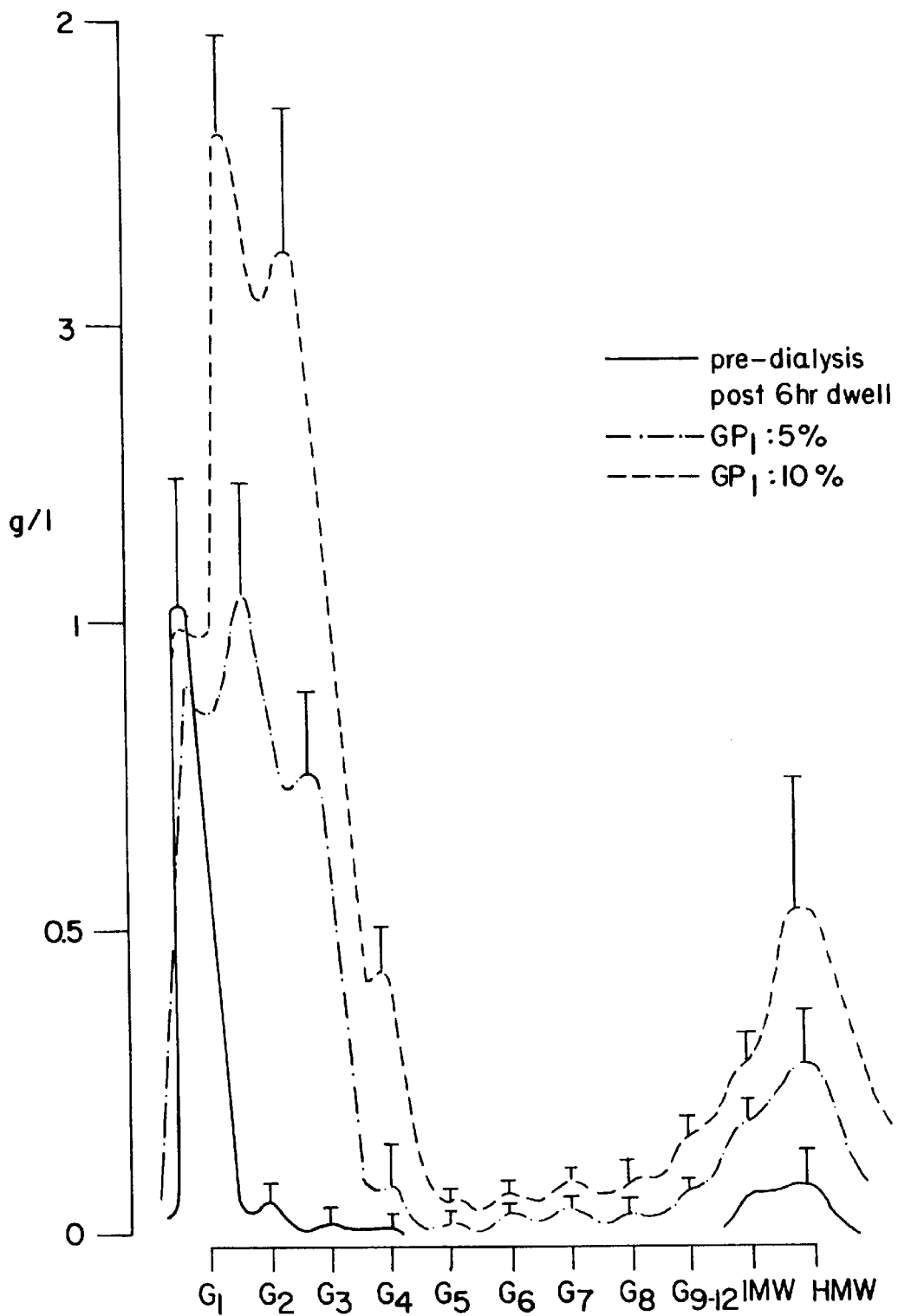

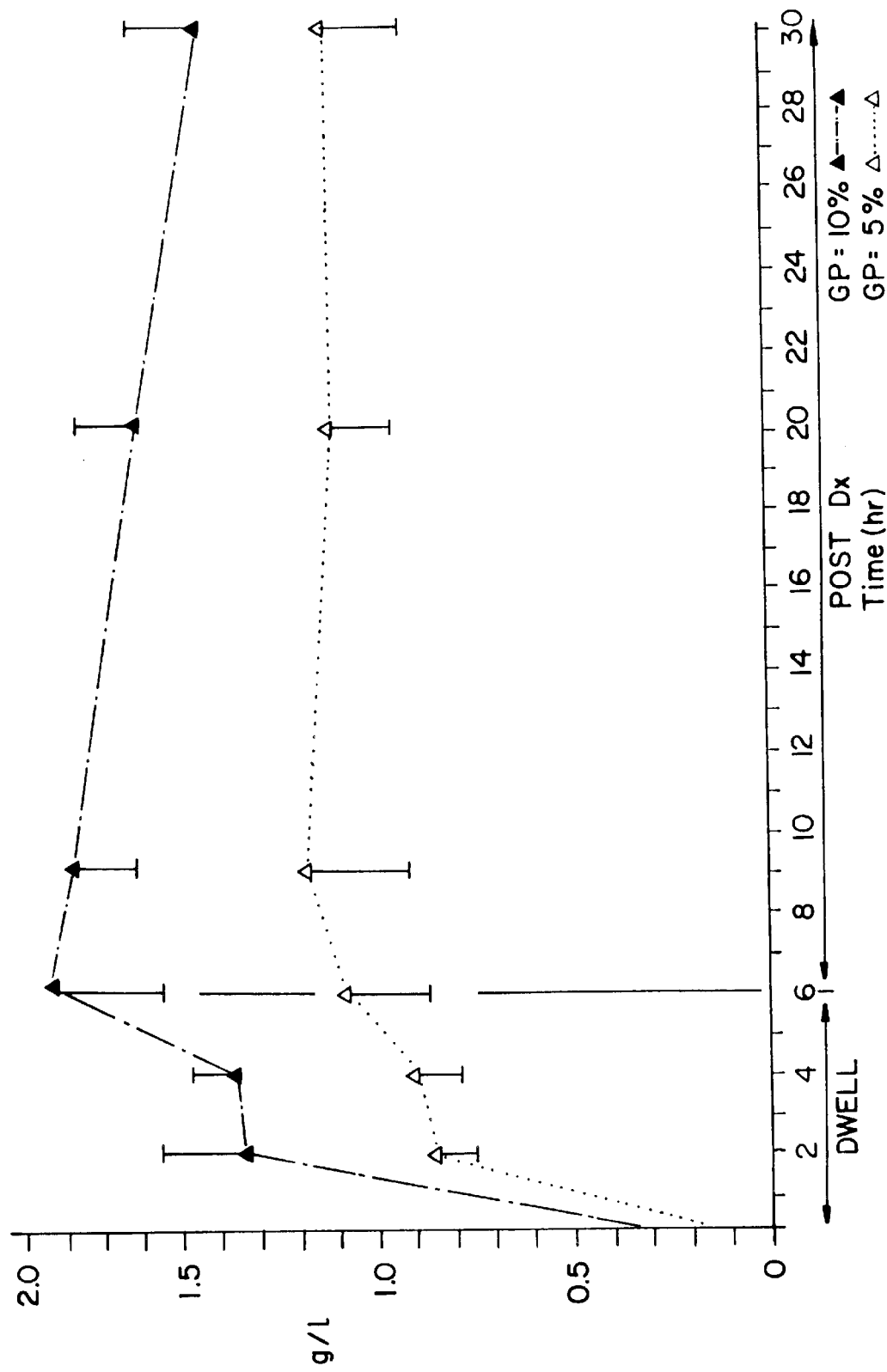

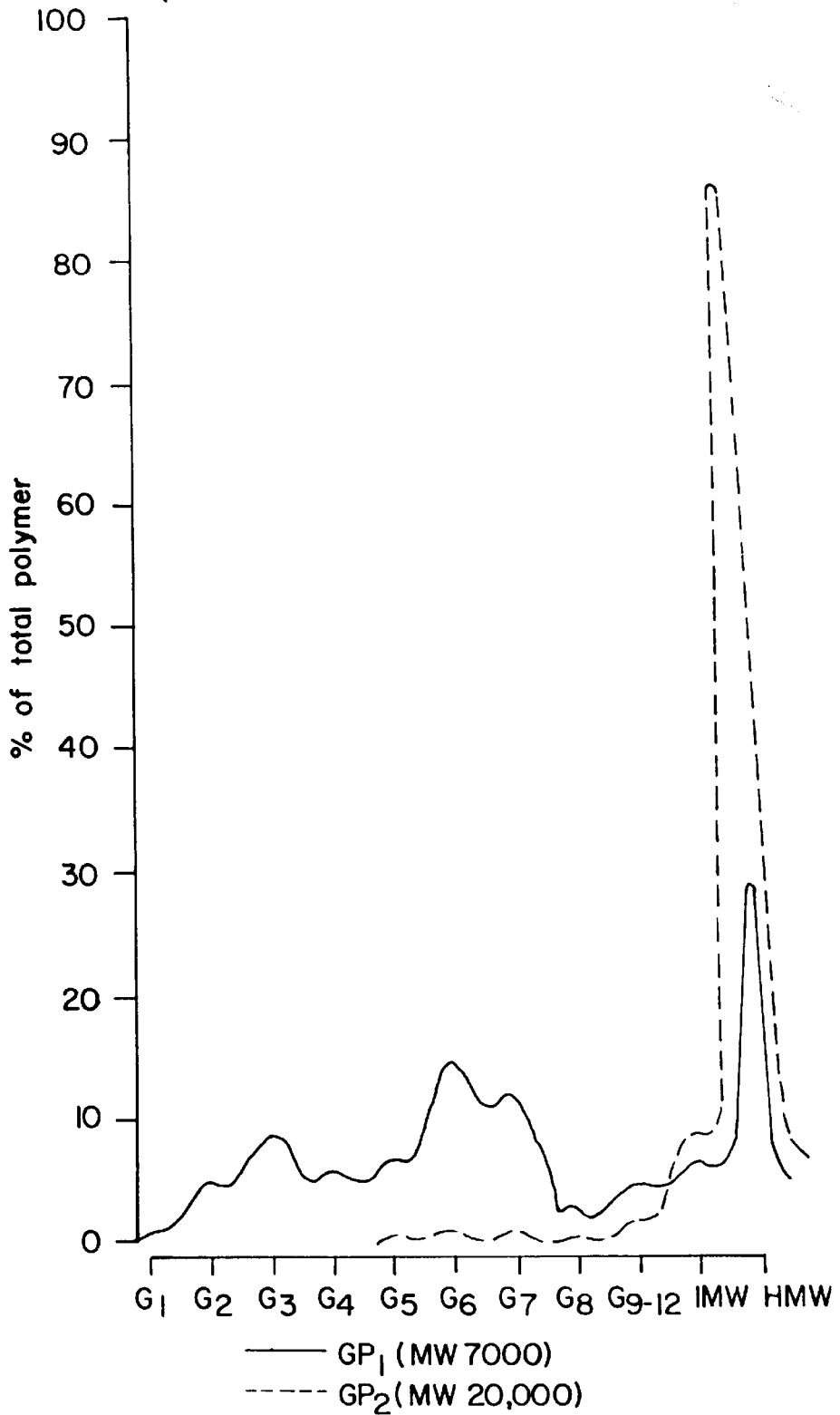

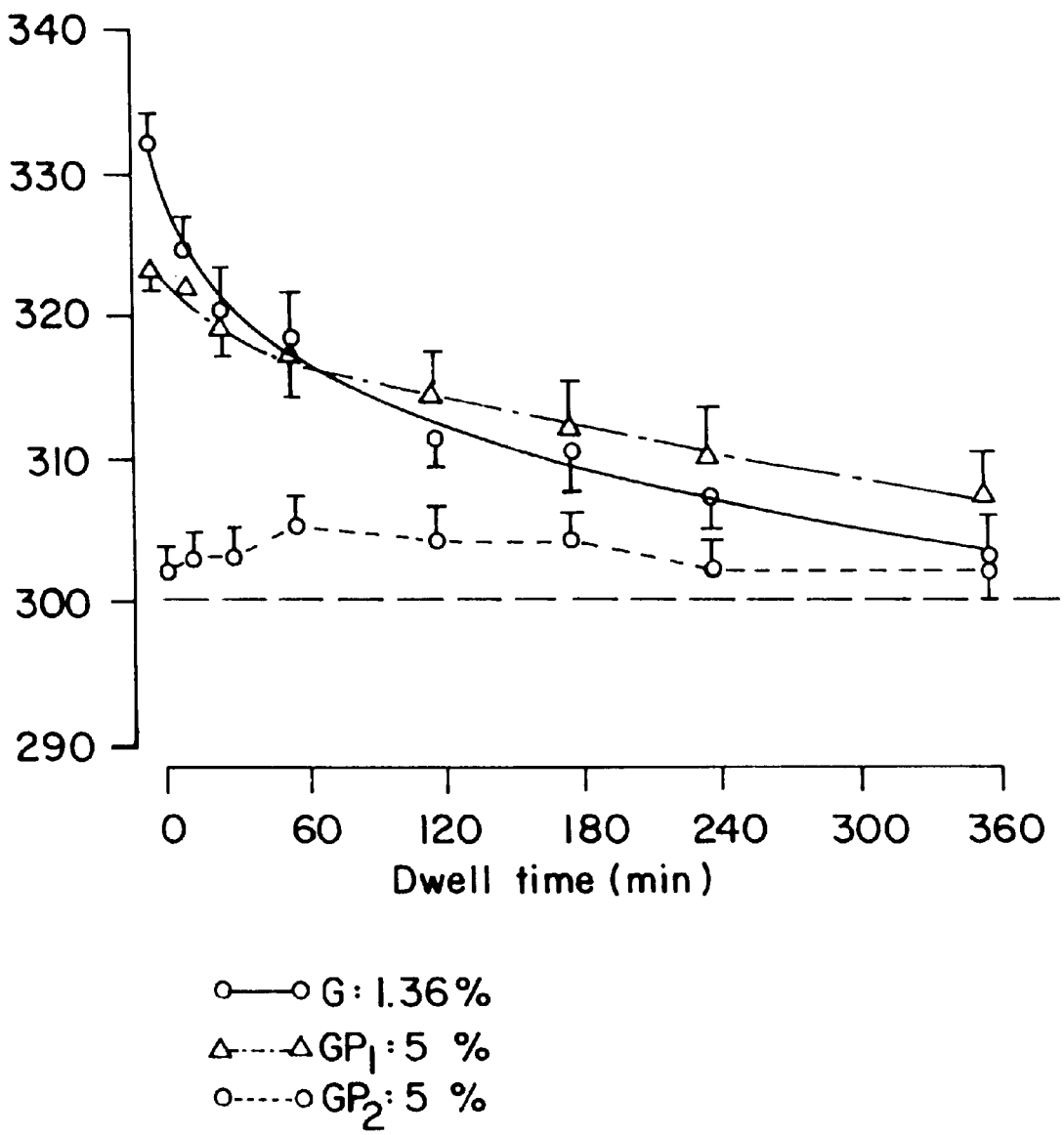

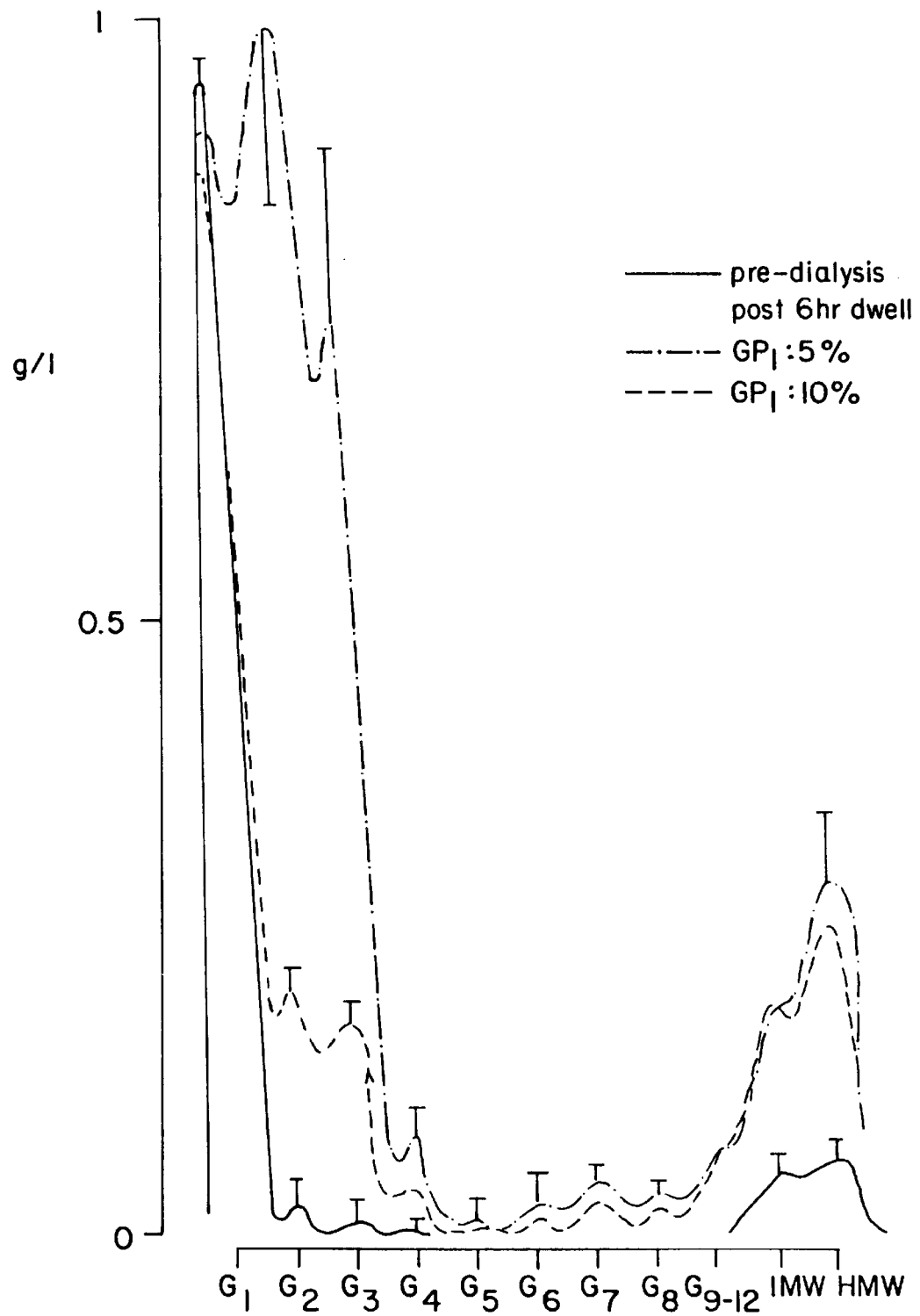

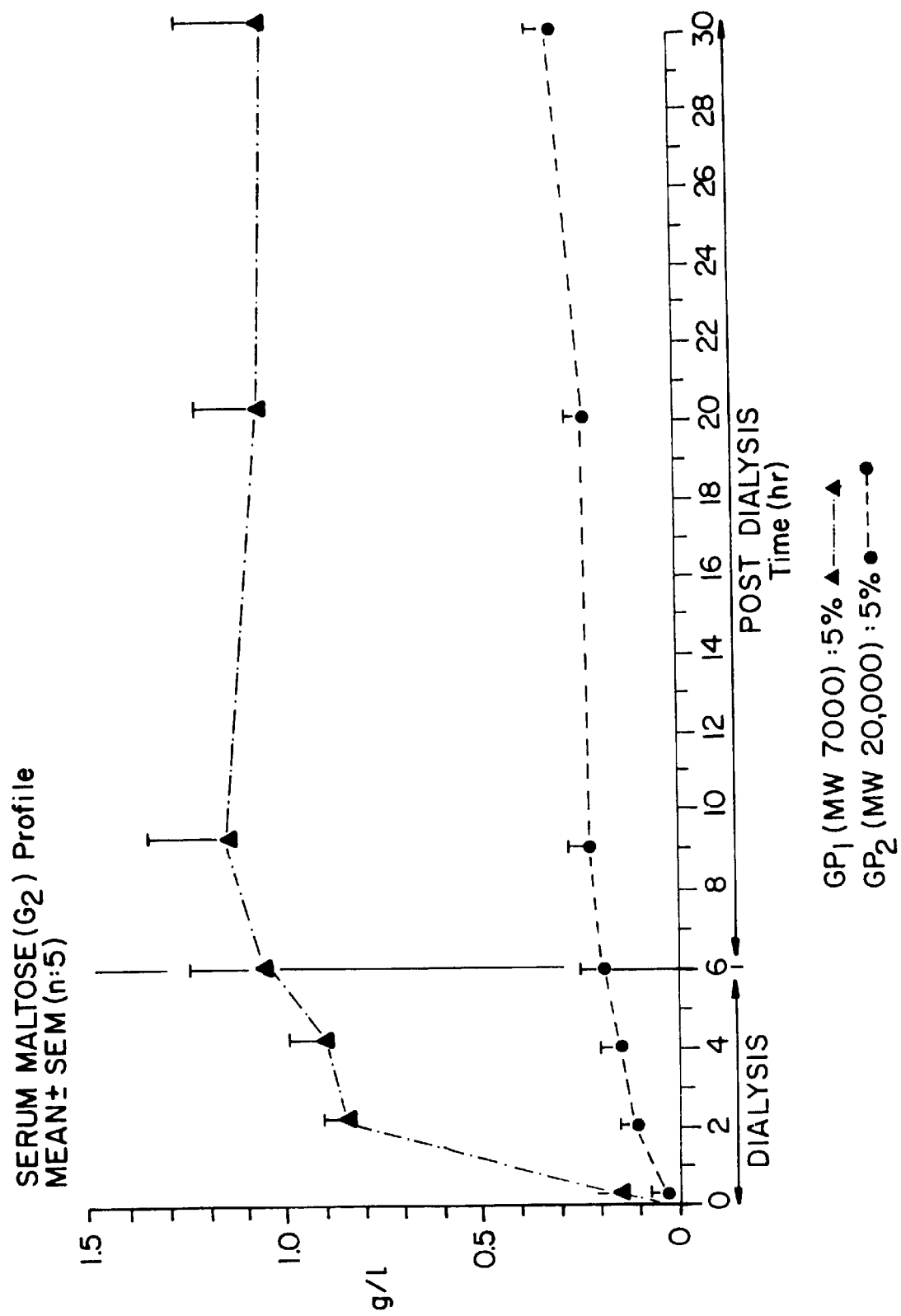

PERITONEAL DIALYSIS AND COMPOSITIONS FOR USE THEREIN

CROSS-REFERENCE TO RELATED APPLICATIONS

This application is a continuation of Ser. No. 335,750, filed Apr. 10, 1989, now abandoned which is a continuation-in-part of Ser. No. 157,720, filed Feb. 19, 1988, now abandoned, which is a division of Ser. No. 891,342, filed Jul. 31, 1986, now abandoned, which in turn is a continuation-in-part of Ser. No. 699,088, filed Feb. 7, 1985, now abandoned, which is a continuation-in-part of Ser. No. 569,760, filed Jan. 10, 1984, now abandoned.

BACKGROUND OF THE INVENTION

1. Field of the Invention

Peritoneal dialysis can be used for treatment of both acute and chronic renal failure. The treatment should ideally serve to restore the composition of the blood of the patient to that which would prevail if the patient's kidneys were functioning normally, and to maintain the blood in such a state. In the present state of the art, such ideal results are not achievable and are probably as some of the normal kidney functions, for example synthesis of hormones and enzymes, are of such a nature that dialysis of any kind cannot be expected to compensate for loss of these functions. However, even with its recognized imperfections, the established technique of carrying out peritoneal dialysis using dextrose as the osmotic agent has been of great value, and any improvement over it is of potential importance.

Peritoneal dialysis is an alternative to haemodialysis. In haemodialysis, the patient's blood is treated outside the patient's body to effect removal of water and waste products, such as urea and creatinine, by subjecting the blood to a process of dialysis in an artificial kidney machine. In peritoneal dialysis the patient's blood is not withdrawn from the body; instead, a dialysis solution is introduced into the abdominal cavity and removal of water and waste products is effected by dialysis across the peritoneal membrane.

In order to create the osmotic pressure which is necessary to cause peritoneal dialysis, the dialysis solution must contain an osmotic agent which has, in the past, normally been dextrose.

It has been recognized for some time that the use of dextrose as the osmotic agent is not entirely satisfactory, mainly because the dextrose can pass from the abdominal cavity through the peritoneal membrane, causing an undesirably rapid drop in the osmotic pressure, so that the dialysis solution has to be removed and replaced by fresh solution more frequently than is desirable, and also causing an increase in the level of dextrose in the blood, which is often injurious to the patient.

2. Background Art

It has previously been suggested that the performance of peritoneal dialysis solutions might be improved if dextrose were replaced, as the osmotic agent, by a mixture of glucose polymers. One such suggestion appears to hive been at a seminar on renal disease at Manchester Royal Infirmary on Jul. 1st, 1981. Subsequently, P.C.T./U.S. Specification No. 82/00774 disclosed a peritoneal dialysis solution comprising a water solution of physiologically tolerable pH, having physiological salts and metabolizable carbohydrate polymers having an average degree of polymerisation (D.P.) of at least 4 in concentrations sufficient safely to effect the removal of solutes and water from a patient by peritoneal dialysis. The polymers may be glucose polymers having an average D.P. of 4 to 10.

U.S. Pat. No. 3,783,100, Larson et al, Jan. 1, 1974

This patent discloses the preparation of high D.E. conversion syrups which are readily filterable and recoverable. Starch is hydrolyzed under superatmospheric conditions and heated to a temperature of at least 250° F. The hydrolyzate is then cooled to a temperature between 185° F. and 200° F. Alpha amylase still continues to break down the hydrolyzate. The resulting product has a D.E. value greater than 5.

U.S. Pat. No. 3,912,590, Slott et al, Oct. 14, 1975

This patent discloses a process for liquefying and thinning starch by treating an aqueous suspension of at least 25 wt. % starch with alpha amylase produced by *B. licheniformis* at a temperature from 100°–115° C.

U.S. Pat. No. 3,928,135, Milner, Dec. 23, 1975

This patent relates to preparations of glucose polymers intended for intravenous injection. As stated in this patent at col. 4, lines 22–30, "The invention also includes the novel glucose polymers that are suitable for intravenous use which comprise a mixture of polymers each of which is substantially no more than 10glucose units long. The difference between this intravenous product and the oral product is that the oral product also contains a proportion, e.g., 10% by weight, of polymers more than 10 glucose units long, and may have present an unspecified number of 1–6 linked units."

U.S. Pat. No. 4,182,756, Ramsey et al, Jan. 8, 1980

This patent relates to the use of glucose polymers having a D.P. ranging from 4–10. Such compositions are used for intravenous administration to human patients.

U.S. Pat. No. 4,239,041, Popovich et al, Dec. 16, 1980

This patent discloses a process and apparatus for continuous ambulatory peritoneal dialysis. Dialysis fluid is passed from a has through a tube which extends through a surgically implanted dacron cuff and into the peritoneal cavity. The used dialysis fluid is collected in another bag connected by another tube to a coupling next to the dacron cuff.

U.S. Pat. No. 339,433, Kartinos et al., Jul. 13, 1982

This patent discloses a peritoneal dialysis solution containing osmolarity increasing agents other than dextrose. Such materials include ethylene maleic acid copolymer resins, carboxymethyl-polysaccharides, carboxymethylpolyvinyl alcohol, polypeptides, proteins, esters of polyvinyl alcohol, polypeptide and carboxylic acid reaction products, hydroxypolycarboxylic acids, polymethylvinyl ether-maleic acid, amino acid and dicarboxylic acid halide reaction products, and predominantly sodium salts of dextran sulfate.

European Patent Application No. 76,355, Ramsey, Apr. 13, 1983

This application discloses a peritoneal dialysis solution comprising glucose polymer, sodium, calcium, magnesium, chloride, lactate, and sodium hydroxide. The average degree of polymerization of the glucose polymer is preferably at least 4, but preferably at least 99% of the glucose polymer molecules should have less than 26 glucose units.

WIPO Application No. WO82/03329, Silk et al, Oct. 14, 1982

This application discloses a glucose polymer preparation consisting predominantly of glucose polymers with a degree of polymerization from 10 to 40. This preparation has a reduced osmotic pressure. The polymers are linked by 1–4 alpha and 1–6 alpha-D-glycosidic chemical bonds.

UK Patent No. 1,280,001, Hayashibara Co., Jul. 5, 1972

This patent discloses a process for preparing amylitol by treating amylopectin with alpha-1, 6-glucosidase to form amylose, dissolving the amylose in water, adding a nickel catalyst to the amylose solution, and then introducing hydrogen at a temperature not more than 100° C. and a pressure up to 100 kg/cm$^2$.

UK Patent No. 1,595,596, Takeda Chemical Industries, Ltd., Aug. 12, 1981

This patent discloses bacterial Beta-1,2-glucans produced by bacteria of the genus Alcaligenes and of the genus Agrobacterium. These glucans have an average degree of polymerization of 170. Hydrolyzates and carboxymethylated derivatives of these glucans are also disclosed. These glucans and their derivatives are used in the treatment of mammalian tumors.

J. Rubin et al, "Substitution of a Starch Polymer for Glucose in Peritoneal Dialysis," *Nephron*, Vol. 39, pp. 40–46 (1985). This article discusses the use in dogs of peritoneal dialysis polymer solutions of maltose and maltotriose, maltotetrose, and maltopentose, in comparison with glucose. The polymers, as shown in Table III of the article, have molecular weights ranges from 319 to 838. The use of these polymers in solution has not shown a clear advantage over the previously used glucose (Cl) solutions.

J. F. Winchester, M.D., et al, "A Comparison of Glucose Polymer and Dextrose as Osmotic Agents in CAPD," *Frontiers in Peritoneal Dialysis*, John F. Maher, M.D., and James F. Winchester, M.D., Editors, Field, Rich and Associates, Inc., New York (February 1986). This article compares peritoneal dialysis solutions of glucose polymers with solutions of dextrose in CAPD. The glucose polymers have an average molecular weight of 710 and a degree of polymerization from 2 to 15. The discussion of the comparisons show that similar results were obtained regarding the clearance of impurities from the blood between the glucose polymer and dextrose solutions. The article does suggest that combining glucose oligosaccharides of higher molecular weights, along with other osmotic agents such as amino acids, may be a useful alternative to dextrose for use in CAPD solutions.

U.S. Pat. No. 4,308,255, Raj et al, Dec. 29, 1981

This patent discloses a balanced oncotic pressure fluid suitable as a dialysate in the treatment of patients suffering from loss of kidney function. The solution comprises about 224 mEg sodium, about 164 mEg chloride, about 72 mEg acetate, about 2 mEg potassium, about 3 mEg calcium, about 2 mEq magnesium, about 6% dextran, about 2% dextrose and about 71 mg zinc gluconate. The ratio of sodium to choride in this solution is about 1.37:1.

Jon Gjessing, "The Use of Dextran as a Dialysis Fluid in Peritoneal Dialysis", *Acta med. scand.* Vol. 185, pp. 237–239, 1969. This article discloses use of a 6% dextran solution (Macrodex) in saline dialysis fluid for peritoneal dialysis. The molecular weight of dextran is 60,000 and the dialysis solution contains no buffers, such as lactate or bicarbonate. On page 239 of the publication, it is stated that the clinical use of dextran solutions for dialysis is principally for patients with diabetes, without oedema or acidosis; and that a dialysis fluid containing dextran, sorbitol, electrolytes, and a small quantity of glucose might prove to be more satisfactory than fluids containing dextran or glucose alone.

UK Patent No. Application No. 2,042,547A, Verwaerde et al, Sep. 24, 1980

This patent application discloses a starch hydrolysate, optionally hydrogenated, whose glucid spectrum displays:

a content of monosaccharides (DP=1) less than 14%;

a content of disaccharides (DP=2) less than 35%, and preferably less than 20%;

a content of oligosaccharides of DP 4 to DP 10 ranging from 42% to 70%, and preferably from 42% to 60%, the oligosaccharides of DP 5 to DP 7 representing a proportion preferably higher than 25% and more preferably higher than 30%;

a content of polysaccharides of DP higher than 10 less than 32%, and preferably less than 25%.

On page 2, lines 54–68, the starch hydrolysates find use in different fields, including the following:

in the preparation of binders for foundry moulds and cores;

in human feeding, notably the manufacture of jams, chocolates, sausages, ice-creams, chewing-gums and hard candies, the foodstuffs in question being moreover non-cariogenic when the starch hydrolysates used are hydrogenated and their content of products of DP higher than 20 is less than 3%;

in infant dietetics, and feeding of medical patients;

in the preparation of polyurletharnes in the make-up of blood plasma substitutes; and in the manufacture of dialysis solutions for the treatment of renal diseases.

SUMMARY OF THE INVENTION

The present invention relates to a peritoneal dialysis solution comprising novel glucose polymer mixtures containing at least 15 wt. % of glucose polymers having a degree of polymerization (D.P.) greater than 12. The invention further relates to a method for preparing such glucose polymers and peritoneal dialysis solutions containing the same.

BRIEF DESCRIPTION OF THE DRAWINGS

FIGS. 1, 2 and 3 describe, respectively, dialysate osmolality profile, serum profile, and rise of maltose for the GP solutions used in Phase 1 of the clinical study.

FIG. 4 describes the molecular weight distribution of a high molecular weight glucose polymer identified as GP2 in Phase 3 of the clinical study.

FIG. 5 describes the relationship between dialysate osmolality and dwell time for GP2 solution in Phase 3 of the clinical study.

FIG. 6 describes the serum glucose polymer profile of the GP2 polymer used in Phase 3 of the clinical study.

FIG. 7 shows that adequate peritoneal clearances can be achieved during peritoneal dialysis when using a GP2 polymer in Phase 3 of the clinical study.

DESCRIPTION OF THE PREFERRED EMBODIMENTS

Figure 1:
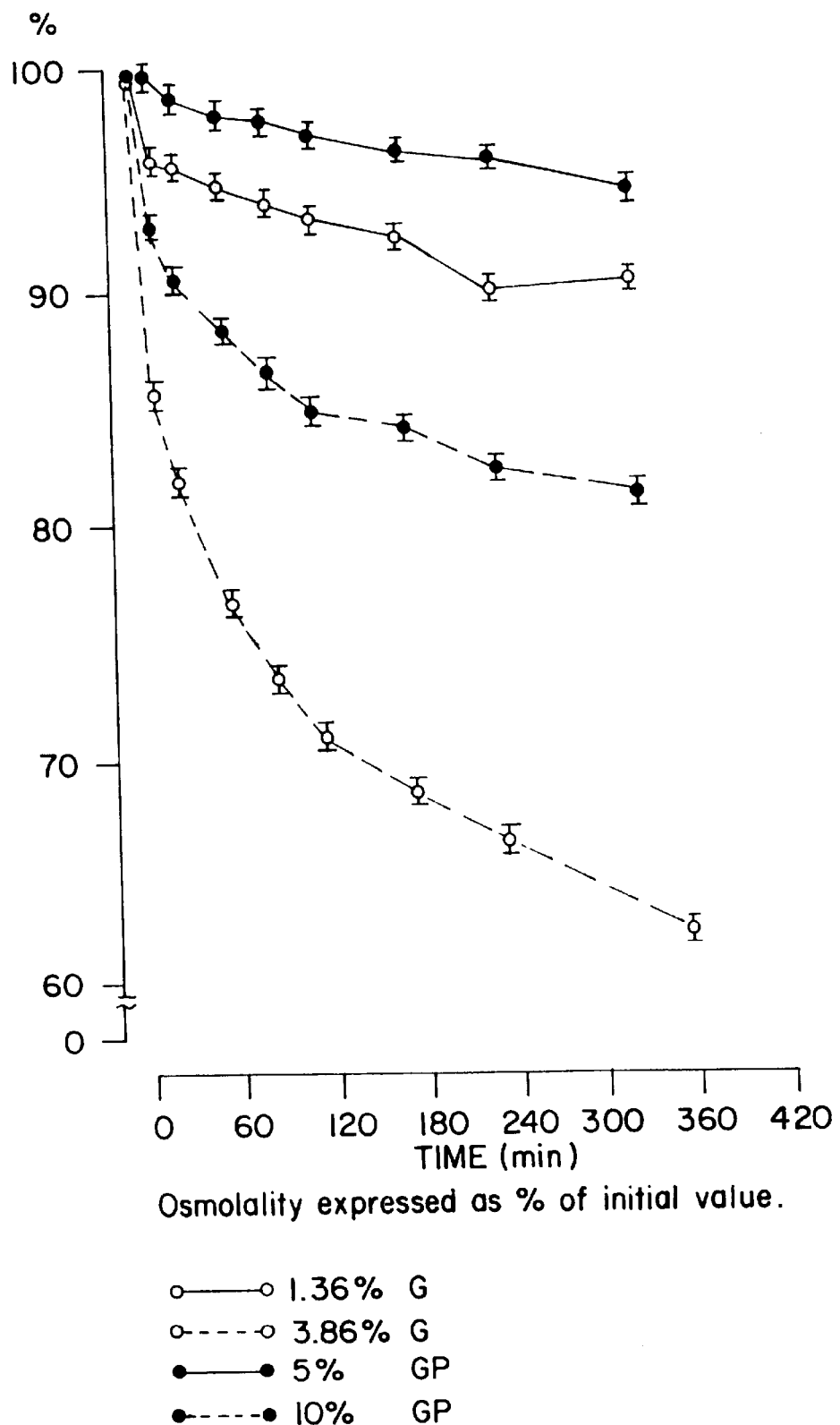

Prior to the present invention it had been thought that glucose polymer mixtures for use in peritoneal dialysis solutions should preferably have little or no content of glucose polymers of relatively high D.P. There were several reasons for this. The concentration of an osmotic agent in a solution which is required to produce a given osmotic pressure is directly related to its molecular weight and it would therefore be expected that with an osmotic agent consisting of a glucose polymer mixture containing a substantial amount of high molecular weight polymers the concentration of the osmotic agent required to produce the desired osmotic pressure would be so high as to make the solution too viscous for it to be of practical value in peritoneal dialysis. This has now been found not to be the case. Another disadvantage that was expected to result from the presence in the osmotic agent of high molecular weight glucose polymers was that passage into the blood of the patient of such polymers would be injurious, at least in the treatment of chronic renal failure, because of an expected inability of the patient to metabolize these polymers as efficiently as glucose polymers of lower molecular weight. This expectation has also proved to be unfounded.

It has been found that it is advantageous to use an osmotic agent which is a glucose polymer mixture containing more than 15%, preferably more than 50% by weight of glucose polymers of D.P. greater than 12.

Firstly, it has been found in clinical tests that glucose polymers of D.P. greater than 12 do not readily pass through the peritoneal membrane during dialysis. As a result, the osmolarity of the dialyzing solution drops less rapidly than would he expected so that the solution can be allowed to remain in the peritoneum for a longer time than would otherwise be feasible. Secondly, the glucose polymers of D.P. greater than 12 are apparently more effective as osmotic agents than would be indicated by calculations based on the standard assumption that each molecule of such a polymer would be osmotically the equivalent of one molecule of dextrose or any other compound. This is demonstrated by the fact that the dialysis solutions of the present invention can be satisfactorily used in peritoneal dialysis with a concentration of glucose polymers in the solutions considerably lower than would have been expected. The dextrose solutions used in the past have commonly contained about 4 or 5% of dextrose. The osmolarity of a solution is normally calculated by reference to the number of molecules in the solution; thus, it would be expected that if the dextrose were replaced by maltose the concentration of maltose (which has a molecular weight almost twice that of dextrose) would need to he about double that of the dextrose, i.e. 8 or 10%. When glucose polymer mixtures of average molecular weight higher than that of maltose were used as the osmotic agent, even higher concentrations would be expected to be necessary. However, it has been found that in practice the dialysis solutions of this invention can create a sufficient osmotic pressure for peritoneal dialysis without substantially increasing the concentration of the glucose polymer mixture above that of dextrose in the solutions previously used. The reason for this is not yet known.

It is well known that glucose polymer mixtures can be prepared by hydrolysis of starch, as disclosed, for example, in British Specifications Nos. 1,444,901 and 2,008,406.

In these known processes, one or more of the process steps is carried out in order to remove carbohydrate material that has too low or too high a molecular weight. Further, the known processes usually comprise a very large number of steps and/or comprise a change in the state (liquid or solid) of the material being treated which make it difficult or impossible to carry out the process continuously.

It has now been found that by more careful control of the enzymatic hydrolysis of the starch, more particularly by carrying out this hydrolysis in two stages in a particular way, little or no undesirable carbohydrate material is produced so that it is not necessary to separate hydrolysis products having too low or too high a molecular weight. The overall process is, consequently, much simplified and is well suited for continuous and substantially automated operation.

According to one aspect of the present invention, there is provided a process for the preparation of a sterile agueous solution of a glucose polymer mixture, the mixture containing less than 5% by weight of glucose and more than 15% by weight of glucose polymers having a degree of polymerisation of more than 12, which comprises (i) gelatinising clean, pre-washed starch containing not more than 5% of 1,6-linkages in aqueous suspension with from 0.05 to 0.13%, based on the weight of the suspension, of at least one thermophilic amylase at a pH of from 6.0 to 6.8 and a temperature of 95° to 100° C., (ii) adjusting the pH of the agueous mixture from step (i) to 4.5 to 5.0 by the addition of a physiologically acceptable organic acid and increasing the concentration of thermophilic amylase to from 0.15 to 0.25%, on the same basis, by the addition of further amylase and effecting dextrinisation of the gelatinised starch at a temperature of 90° to 95° C. so as to obtain a hydrolysis product predominantly consisting of glucose polymers having a degree of polymerisation of more than 12 and containing less than 1% by weight of glucose and less than 2% by weight of each of maltose and maltotriose, (iii) adjusting the pH of the agueous mixture from step (ii), if required, to 3.5 to 4.5 by the addition of a physiologically acceptable organic acid and effecting hydrolysis of the dextrinised starch at a temperature of 65° to 75° C. by means of a bacterial alpha-amylase which is capable, under these conditions, of producing less than 5% of glucose, based on the weight of the dextrinised starch, and continuing hydrolysis under these conditions until a glucose polymer mixture of the desired composition is obtained, and (iv) adjusting the pH of the agueous mixture from step (iii) to 2.0 to 3.0 by the addition of a physiologically acceptable organic acid and heating the mixture at a temperature of 96° to 100° C. so as to inactivate the enzymes.

It has been further found that by appropriate choice of the amount of bacterial alpha-amylase used in step (iii), glucose polymer mixtures having a varying distribution of polymer sizes can be obtained, as will be illustrated in the Examples given below.

These varying polymer size distributions can be obtained by using concentrations of the bacterial alpha-amylase of from about 0.1 to about 3.0%, based on the total weight of the agueous mixture.

The process according to the invention is preferably carried out so as to produce a relatively concentrated solution of the glucose polymer mixture, that is containing 65 to 80% w/v, of the polymer mixture; such solutions having a specific gravity of from 1.275 to 1.300. With the addition of a conventional amount of a physiologically acceptable preservative, for example 0.1% by weight of sodium benzoate, and packaged in a sealed container under sterile conditions, such solutions are storage stable at temperatures of from 0 to 100° C. for up to 2 years. When the containers are opened, the solutions are usable, when kept at room temperature, for up to 2 months.

The solutions just described, that is containing 65 to 80% w/v of a glucose polymer mixture having one of the preferred polymer mixture compositions described, are novel and constitute a further aspect of the present invention.

The process according to the invention will now be described in greater detail.

The starch used as the starting material of the process should, as stated, be a clean, pre-washed starch containing not more than 5% of 1,6-linkages. The starch may be derived from corn, rice or barley, corn starch being in general the most readily available. In the United States, so-called "green" starch is commercially available, this being an agueous suspension of washed corn starch, and this is also a suitable starting material.

The washed starch should be low in sodium, that is contain less than 5 milliequivalents of sodium per 100 g., and low in proteins, that is contain less than 0.1% of protein. The starch should be assayed for insecticides, weedkillers, and plant hormones and should be free of these products.

Clean, pre-washed starch meeting the requirements specified is commercially available from a number of suppliers.

The initial agueous suspension preferably contains from 50 to 60% by weight of starch; with evaporative losses of water during the various stages of the process, this range of initial solids concentrations gives the above-mentioned preferred solids content, i.e. 65–80% by weight of the final solution.

Step (i) of the process is preferably carried out with approximately 0.1% of the thermophilic amylase at a pH of approximately 6.0 and a temperature of approximately 98° C. A number of thermophilic amylases are commercially available and any of them can, in principle, he used in steps (i) and (ii). Suitable amylases include, for example, those available under the trade names "Termamyl" and "Fungamyl" from Novo, Denmark; of these "Termamyl" is particularly preferred.

Step (i) of the process, the gelatinisation of the starch, is completed quite rapidly, for example in 5–10 minutes.

To effect step (ii), the dextrinisation of the gelatinised starch, the concentration of the amylase is substantially increased, preferably doubled, to within the range 0.15 to 0.25%, and a slightly lower temperature, preferably approximately 95° C., and a lower pH, preferably about 4.5, is used. The organic acid used to effect the reduction in the pH (and also for steps (iii) and (iv)) may, for example, be citric acid, lactic acid or acetic acid, of which the first is preferred.

Step (ii) takes considerably longer than step (i); the former typically takes from 2–4 hours.

The mixture is then passed on to step (iii). The pH is reduced, if required, to within the range 3.4–4.5, preferably to approximately 4.5, and a lower temperature, that is 65°–75° C., preferably approximately 70° C., is used. At these temperatures, thermophilic amylases are substantially inactive and a bacterial alpha-amylase which is active at these temperatures and which is capable of producing less than 5% of glucose, based on the weight of the dextrinised starch, is used. A particularly preferred bacterial alpha-amylase for this purpose is that available under the trade name "Ban" from Novo, Denmark, but other suitable bacterial alpha-amylases can be used, if desired. Step (iii) typically takes about 4 hours.

In step (iv), the pH is again reduced, preferably to a pH of approximately 2.5, and the agueous mixture is heated at a temperature of 96° to 100° C., preferably approximately 98° C., to effect complete deactivation of the enzymes. This step typically takes about 3 hours.

It is preferred, but not essential, to filter the agueous mixture between steps (ii) and (iii). A fine pore glass filter is preferred, for example having a porosity of 1H.

It will be appreciated that since there is no removal of unwanted products in the process according to the invention, it can readily be carried out continuously using a number of reactors or tanks connected in series, each step being carried it out in a separate reactor and with means for metering the required amounts of enzyme and acid to the various steps and means for thermostatically controlling the temperature in the reactors. Such a process is well suited to automated control.

The final product may be discharged directly from the final reactor or tank to a sterile filling station where it is filled into suitable containers, such as plastics sachets, which are then sealed.

The amylases used in the process according to the invention sometimes impart an undesirable odour or flavour and/or discoloration to the product and for this reason it is desirable to use the minimum amount of amylase (within the ranges specified above). If, despite this precaution, the product is subject to an undesirable odour or flavour and/or discoloration, it can readily he de-odorised and/or de-colourised by contact with a suitable inert absorbent or adsorbent, such as activated carbon.

It is also preferred to add a small amount of a permitted preservative, for example 0.1% by weight of sodium benzoate, prior to packing.

The solutions of glucose polymer mixtures obtained by the process according to the invention are completely non-antigenic.

The glucose polymer solution is generally within the pH range of 4.5 to 7.5, preferably a pH within the range of 6.8 to 7.2, which is preferably adjusted to a pH of 7.0, in this case preferably with sodium acetate, and electrolytes are added thereto, prior to sterile packing. The concentrated solution can be diluted when required to give a peritoneal dialysis solution having an appropriate concentration of glucose polymers. The dilution can be effected by means of an agueous diluent containing any solutes known to be desirable in peritoneal dialysis solutions, such as lactates, acetates and amino acids, the particular composition of the diluent being at the discretion of the clinician.

If lactates or acetates are employed in the glucose polymer solution, a typical concentration is 30 to 45 m Eg/liter. Other physiological ions such as magnesium, potassium, and carbonate as well as other desirable beneficial additives may be present. For example, 0.5 to 25 g/liter of amino acid salts or protein hydrolyzates may be added to enhance further the ultrafiltration of water into the peritoneal dialysis solution by their natural osmotic effect, as well as serving as a source of supplemental nitrogen for protein for the patient as they diffuse into the bloodstream. This can counter-balance any protein loss by the patient during the peritoneal dialysis procedure, or may serve as the prime source of protein nutrition for the patient. The use of amino acids in peritoneal dialysis solutions is taught in the preliminary communication on page 812 of the Oct. 12, 1968 issue of the *Lancet*. This article, however, does not teach the use of metabolizable carbohydrate polymers in peritoneal dialysis solutions.

A typical peritoneal dialysis solution contemplated for use is a sterile water solution which may contain, for example, from 116 to 145 mEg/liter of sodium; from 0 to 6 mEg/liter of calcium, from 90 to 144 mEg/liter of chloride, about 1 to 2 mEg/liter of magnesium and from 2 to 15% w/v of the glucose polymer as described herein. It is also desirable for from 30 to 40 mEg/liter of bicarbonate precursors such as one or more of lactate, acetate, malate, and/or succinate ions to be present. The bicarbonate precursor acid ions mentioned above, as well as other acid ions of the Krebs cycle may he added to also offer advantages in pH control of the peritoneal dialysis solution of this invention. The sodium or potassium salts of such ions, for example, may he used for this purpose, or the free acids.

Alternatively, a concentrated solution of the glucose polymer mixture may be spray-dried to produce a powdered form of the mixture which can, when desired, be dissolved in a suitable agueous solution to form a peritoneal dialysis solution.

The concentration of the glucose polymer mixture in the peritoneal dialysis solutions of the invention is varied in accordance with the nature of the required therapy and may, for example, range from about 2% to about 15%. The upper limit of the concentration is subject to keeping the viscosity of the solution low enough so that it will pass through he smallest bore of the dialysis apparatus being used for introducing and withdrawing the solution from the peritoneum. The lower limit is dependent on establishing a gradient of osmotic pressure between the serum and peritoneum sufficient to achieve desired clearances of water and waste products from the serum but not so great as to effect too rapid a rate of withdrawal of water. For use in continuous ambulatory peritoneal dialysis a concentration of from 2 to 5% is generally appropriate, with a dwell time in the abdominal cavity of from 5 to 8 hours. For treatment of acute renal failure a concentration of from 5 to 10%, with dwell times of up to 6 hours, is indicated. In a situation where rapid withdrawal of water is of paramount importance concentration of 10 to 15% may be desirable. These figures are given only as a general guide because ultimately the choice of the composition of the peritoneal dialysis solution most suited to the needs of a particular patient must rest with the clinician.

Although it is not yet clear why the use of an osmotic agent comprising a glucose polymer mixture including a relatively high proportion of high molecular weight material is advantageous it seems likely that this is due to a phenomenon, which may be described as colloidal osmosis, caused by the apparent ability of the high molecular weight material to continue attracting water and its solutes across the peritoneal membrane for a longer period than lower molecular weight material would do. Presumably, this is partially because of the relative inability of the high molecular weight polymers to diffuse through the peritoneal membrane hut it may also derive from hydrogen bonding between water molecules and the higher molecular weight polymers which in effect serves to be equivalent to removal of water from the dialysate in the abdominal cavity. Such hydrogen bonding would also tend to diminish the ability of the molecules to pass through the peritoneal membrane in that it would increase the size and the diameter of the molecules.

One of the advantages of the osmotic agents used in the present invention is that they are capable of sustaining an osmotic pressure gradient across the peritoneal membrane for longer periods than has been feasible when using dextrose as the osmotic agent. Because of the rapid decay of the osmotic pressure gradient when using dextrose, it has beer necessary to use dialysis solutions having a relatively high initial osmolality. The osmolality of human blood is of the order of 300 mOsm/kg. In order to minimize stress on the peritoneal membrane it is desirable that the osmolality of the dialysis solution should exceed that of the patient's blood by as little as is compatible with achieving satisfactory dialysis. The preferred osmolality of the dialysis solutions of this invention will range from about 265 to 378. The compositions of the present invention make it possible to achieve satisfactory dialysis with an initial osmolality of the dialysis solution considerably less than when the osmotic agent is dextrose or when it is a glucose polymer containing a substantial Proportion of oligosaccharides, and at the same time to sustain dialysis for longer periods than with previously used dialysis solutions.

As stated above, the glucose polymer mixture used as the osmotic agent includes at least 15% by weight of glucose polymers of D.P. greater than 12 and may include from 20 to 50% of glucose polymers of D.P. greater than 12. The present invention further provides a peritoneal dialysis composition containing an osmotic agent comprising a glucose polymer mixture, said mixture including more than 50% by weight of glucose polymers of D.P. greater than 12. For many purposes, the mixture may contain from 50 to 90% by weight of glucose polymers of D.P. greater than 12. For the treatment of patients in respect of whom it is desirable to keep to a minimum the transfer of carbohydrate from the peritoneum to the serum it is advantageous to use a mixture containing from 75 to 100%, preferably 90 to 100%, by weight of glucose polymers of D.P. greater than 12. The average molecular weight of the glucose polymer mixtures will generally be within the range of 7,000 to 36,000; however the average molecular weight of the polymer mixture is preferably from 15,000 to 25,000, more preferably 18,000 to 22,000 (as determined by high pressure liquid chromatography). Some such glucose polymer mixtures can be produced by the process of the invention but, in cases where this is not so, the desired distribution of polymers can be achieved by fractionation techniques well known in the art of producing glucose polymer mixtures.

The process of the invention produces glucose polymer mixtures containing less than 5% of glucose; such a concentration of glucose is desirable, especially as many patients needing peritoneal dialysis are diabetic. However, if the needs of a patient are such that a higher concentration of glucose is desirable it is a simple matter to add dextrose to the solutions of the invention to whatever extent is appropriate. For most purposes, however, it is desirable that the glucose polymer mixture should contain less than 5%, preferably less than 3% by weight of glucose.

The content of free glucose in the compositions of the invention is within the discretion of the clinician. The glucose polymer mixtures commonly contain from 0–3% by weight of glucose but higher amounts may be present if the needs of the patient so dictate.

The mode of use of the dialysis solutions according to the invention is similar to that of known dialysis solutions. The solution is infused into the peritoneum and allowed to remain there for a predetermined time, after which it is withdrawn and replaced by fresh solution. With the solutions of the present invention it has been found that the dialytic effect is maintained for a longer time than has been the case for most known dialysis solutions. This offers the possibility of achieving adequate clearances of water and waste products from the patient with administration of fewer infusions than has been required in the past, a matter of particular importance in C.A.P.D. where the less frequently the dialysis solution has to be changed the less chance there is of infection (which occurs chiefly during the replacement of spent solution by fresh solution).

In favourable cases it is possible for peritoneal dialysis solutions of the present invention to be allowed usefully to remain in the peritoneum for as long as eight hours. The daily regimen for a patient suffering from chronic renal failure and being treated by continuous peritoneal dialysis then involves three exchanges per day. Each infusion is of two litres in volume so the total infusion per day is six litres. The total amount of fluid withdrawn per day is 7.2 litres, corresponding to a clearance of 5 ml/minute, for components in respect of which equilibrium is achieved between dialysate and plasma.

When treating a patient suffering from acute renal failure (or suffering from poisoning from a drug overdose, as will be discussed below), it is feasible to establish a regimen involving infusion of three litres per hour, withdrawing about four litres at the end of each hourly period, corresponding to a clearance of nearly 70 ml/minute. This is lower than the clearance rate which can be achieved by haemoperfusion, which is of the order of 100 ml/minute. However, haemoperfusion cannot be continued for very long; in some cases a period of up to six hours is as long as can be tolerated without risk. By contrast, peritoneal dialysis can be continued for a very much longer time without such risk.

In order that the invention may be more fully understood, the following examples set forth the best mode now contemplated for carrying out the invention.

EXAMPLES 1–3

A commercially available clean, pre-washed soluble corn starch was suspended in water with agitation to give a 60% by weight suspension.

Step (i), gelatinisation, was carried out in the presence of 0.1%, based on the weight of the suspension, of "Termamyl" thermophilic amylase at a pH of 6.0 and a temperature of 98° C. for 5 minutes, in a first reactor.

The mixture from step (i) was passed to a second reactor and citric acid was metered into it to reduce the pH to 4.5 and additional "Termamyl" was added to raise its concentration to 0.2%, on the same basis. Step (ii), dextrinisation, was carried out at a temperature of 95° C. for 4 hours.

The mixture from step (ii) was then passed to a third reactor in which step (iii), hydrolysis, was effected with "Ban" amylase at a pH 4.5.

Different amounts of the enzyme were used in each example and the conditions used and the polymer composition of the products obtained are summarized in Table 1 below.

TABLE 1

|  | Ex. 1. | Ex. 2. | Ex. 3. |
|---|---|---|---|
| Initial solids, w/v | 70% | 70% | 70% |
| pH | 4.5 | 4.5 | 4.5 |
| Temp. | 70° C. | 70° C. | 70° C. |
| "Ban" enzyme | 0.12% | 0.6% | 3.0% |
| Reaction Time | 4 hrs. | 4 hrs. | 4 hrs. |

The mixtures from step (iii) were then passed to a fourth reactor and citric acid was metered into them to give a pH of 2.5. In the fourth reactor step (iv) was carried out by heating to 98° C. for 3 hours.

The solids content of the final solutions was analyzed and the results obtained are summarized in Table 2 below (G1=glucose G2=polymer with 2 glucose units, G3=polymer with 3 glucose units, etc.)

TABLE 2

| | Examples 1–3 | | |
|---|---|---|---|
| Weight % | Ex. 1. | Ex. 2. | Ex. 3. |
| G1 | 1.4 | 2.6 | 4.0 |
| G2 | 6.8 | 11.0 | 16.6 |
| G3 | 11.3 | 17.6 | 26.2 |
| G4 | 6.9 | 8.9 | 10.6 |
| G5 | 8.1 | 13.0 | 11.5 |
| G6 | 16.8 | 14.7 | 5.1 |
| G7 | 10.2 | 2.3 | 1.8 |
| G8 | 1.7 | 1.3 | 2.0 |

TABLE 2-continued

| | Examples 1–3 | | |
|---|---|---|---|
| Weight % | Ex. 1. | Ex. 2. | Ex. 3. |
| G9 | 0.8 | 1.6 | 1.9 |
| G10 | 0.8 | 1.4 | 1.7 |
| G11 | 0.8 | 1.3 | 1.4 |
| G12 | 0.8 | 1.2 | 1.1 |
| G13–14 | 5.9 | 6.4 | 7.2 |
| G15 and over | 27.2 | 16.7 | 8.7 |

It can be seen that the products of Examples 1, 2 and following compositions:

| Weight % | Ex. 1. | Ex. 2. | Ex. 3. |
|---|---|---|---|
| Glucose | 1.4 | 2.6 | 4.0 |
| D.P. greater than 12 | 33.1 | 23.1 | 15.9 |
| D.P. 2–7 | 60.1 | 67.5 | 71.8 |

EXAMPLE 4

Three further runs using the conditions of Example 1 were carried out to test the consistency of the results obtained The composition of the polymer mixture obtained in each of the three runs is shown in Table 3 below.

It is clear from this table that the process gives remarkably consistent results.

TABLE 3

| Weight % | Run 1 | Run 2 | Run 3 |
|---|---|---|---|
| G1 | 1.5 | 1.5 | 1.4 |
| G2 | 6.6 | 6.8 | 6.8 |
| G3 | 10.8 | 11.4 | 11.3 |
| G4 | 6.6 | 6.9 | 6.9 |
| G5 | 8.2 | 8.1 | 8.1 |
| G6 | 15.9 | 16.7 | 16.8 |
| G7 | 10.4 | 10.4 | 10.0 |
| G8 | 2.5 | 1.7 | 1.7 |
| G9 | 1.3 | 0.9 | 0.8 |
| G10 | 1.0 | 0.9 | 0.8 |
| G11 | 1.0 | 0.9 | 0.8 |
| G12 | 0.9 | 0.8 | 0.8 |
| G13–14 | 6.4 | 6.0 | 5.9 |
| G15 and over | 26.9 | 26.9 | 27.4 |

EXAMPLE 5

A glucose polymer mixture was prepared by a process similar to that of Example 1 except that step (iii) was effected using 0.1% of the "Ban" enzyme. The composition of the polymer mixture obtained was as follows:

| Weight % | |
|---|---|
| G1 | 1.1 |
| G2 | 5.5 |
| G3 | 9.6 |
| G4 | 6.2 |
| G5 | 6.8 |
| G6 | 15.6 |
| G7 | 11.8 |
| G8 | 2.9 |

-continued

| Weight % | |
|---|---|
| G9 | 1.3 |
| G10 | 1.0 |
| G11 | 0.8 |
| G12 | 0.9 |
| G13–14 | 5.5 |
| G15 and over | 31.2 |

It will be seen that the mixture comprised 1.1 wt. % of glucose, 36.7 wt. % of polymers of D.P. greater than 12 and 55.5 wt. % of polymers of D.P. from 2 to 7.

The mixture was used to replace dextrose in a conventional peritoneal dialysis solution and the resulting solution was clinically tested. The tests were carried out on solutions containing respectively 15%, 10% and 5% of the glucose polymer mixture on a weight to volume basis. The 15% solution withdrew water from the blood of a patient at such a rapid rate (about one litre in half an hour) as to cause discomfort in the patient, and the test was discontinued. Such a rapid withdrawal of water is in any case undesirable in the treatment of a patient suffering from chronic renal disease, when dialysis needs to be effected continuously and the rate of withdrawal of water from the blood plasma should ideally he such as to maintain the water content of the plasma at a level comparable with that of a person having normal kidney function. The 10% solution performed more satisfactorily although here again the clearance of water was somewhat more rapid than would usually be appropriate for treatment of chronic renal failure. The 5% solution was more nearly suitable to effect withdrawal of water at the rate of about 1.0 ml per minute which was deemed to be appropriate for the patient concerned, although it seemed likely that a concentration of lower than 5% might actually be feasible and even preferable.

All of the solutions achieved clearances of water, urea, creatinine, uric acid and phosphates as good or better than could be achieved by a similar solution containing 5% of dextrose instead of the glucose polymer mixture. Surprisingly, it was observed that the clearances of urea, creatinine, uric acid and phosphates were almost as good with the 5% solution as with the 10% solution. This indicates that in general a solution containing 5% or less of the glucose polymer mixture would be preferable for use in continuous ambulatory peritoneal dialysis (where treatment is on a 24 hours per day, seven days per week basis) whereas the 10% and 15% solutions would be more appropriate for intermittent treatment where a more rapid rate of withdrawal of water is tolerable or even desirable.

Clearly, the use of such a glucose polymer mixture in peritoneal dialysis represents a considerable step forward in the art. Nevertheless, it was not reasonably to be expected that the dialysis solutions containing these glucose polymer mixtures as the osmotic agent would be equally good for all clinical purposes. In particular, the performance of a dialysis solution can in general be regarded as less critical when it is used in intermittent peritoneal dialysis, for example in treatment of acute renal failure, than when it is used in continuous peritoneal dialysis, because a patient undergoing the latter treatment may be subject to a cumulative effect of any shortcoming of the treatment.

It has been observed that when using a solution containing 10% or more by weight of the glucose polymer composition of Example 5 there is, in some patients, a significant loss of oligosaccharides from the peritoneum. (Oligosaccharides are herein defined as glucose polymers of D.P. from 2 to 10 inclusive.) This was reflected in raised levels of maltose and maltotriose in the serum. On discontinuing dialysis, it was found that the serum maltose level fell only slowly over a period of eighteen hours, suggesting that there had been storage of oligosaccharides. Assessment of the behaviour of the glucose polymers of a molecular weight higher than that of the oligosaccharides, by measurement of the concentrations of these in both the serum and the peritoneum, revealed that there was good retention of these in the peritoneum with minimal appearance of them in the serum.

Although the dialysis compositions of Example 5 are plainly superior to similar compositions containing dextrose as the osmotic agent, it is of course desirable to provide peritoneal dialysis compositions which further reduce the possibility of transfer of carbohydrate from the peritoneum to the serum.

In the case of patients being treated by continuous peritoneal dialysis, it is particularly desirable that the content of oligosaccharides in the glucose polymer mixture should be kept at a level low enough to ensure that too great a storage of carbohydrate does not occur, due to transfer of oligosaccharides from the peritoneum to the serum. Different patients have different requirements in this respect but it is desirable that for patients undergoing continuous treatment, especially those on C.A.P.D. (continuous ambulatory peritoneal dialysis) the oligosaccharide content of the glucose polymer mixture should be no higher than 10% by weight, the mixture containing from 90 to 100% by weight of glucose polymers of D.P. greater than 10.

Such glucose polymer mixtures can he produced by hydrolysis of starch in known manner, followed by treatment of the mixture of glucose polymers so obtained in order to remove some or all of the glucose polymers of lower molecular weight. Preferably, a glucose polymer mixture is prepared by the process described in Example 5 and removal of lower molecular weight polymers is then effected by known fractionation techniques, such as solvent fractionation, or separation of the polymers with the aid of permeable membranes of appropriate cut-off characteristics.

In general, the fractionation techniques employed are such as to remove mainly the lower molecular weight polymers. If desired, however, they may also be used to remove very high molecular weight polymers if this is found to be necessary in order to ensure that all of the final mixture of glucose polymers is sufficiently water-soluble for there to he no tendency for higher molecular weight polymers to precipitate from solution on standing. Precisely fractionates individual glucose polymers having a molecular weight within the range of 7,000 to 36,000 may also be used. It is further contemplated that the high molecular weight polymers can be admixed with glucose or lower molecular weight glucose polymers (D.P. 2 to 10) to provide a peritoneal dialysis composition containing at least 15% by weight of glucose polymers of D.P. greater than 12.

EXAMPLE 6

The glucose polymer mixture of Example 5 was washed repeatedly with agueous ethanol to remove lower molecular weight glucose polymers in the filtrate. Chromatographic analysis of the solid residue showed that after two such extractions the glucose polymer mixture contained less than 5% by weight of polymers of D.P. of 12 or less. After removal of pyrogens (by passing a solution of the glucose polymer mixture through a column of activated charcoal) this glucose polymer mixture was suitable for use as the osmotic agent in a peritoneal dialysis composition according to the present invention.

EXAMPLE 7

The glucose polymer mixture of Example 5 was dissolved in water. To this solution was added 95% w/w ethanol with continuous stirring until a concentration of 55% ethanol was reached. The precipitated higher molecular weight polymers were then separated by decantation. A portion of this separated syrup was analysed and was found to have the following composition:

| | Weight % |
|---|---|
| G1 | 0.5 |
| G2 | 1.2 |
| G3 | 1.4 |
| G4 | 1.1 |
| G5 | 1.9 |
| G6 | 3.6 |
| G7 | 2.2 |
| G8 | 0.7 |
| G9 | 0.5 |
| G10 | 0.4 |
| G11 | 0.3 |
| G12 | 0.3 |
| G13–14 | 7.2 |
| G15 and over | 79.1 |

Thus, the polymer mixture (which would he capable of use as an osmotic agent according to the invention) contained 86.3 wt. % of polymers of D.P. greater than 12 and 13.5 wt. % of polymers of from D.P. 1 to 10.

The remainder of the separated syrup was redissolved in water and re-precipitated by addition of 95% w/w ethanol, this time to achieve a concentration of 65% ethanol. The precipitate was then dissolved in water and the solution was evaporated dryness. The composition of the glucose polymer mixture obtained was as follows:

| | Weight % |
|---|---|
| G1 | — |
| G2 | 0.7 |
| G3 | 0.9 |
| G4 | 0.6 |
| G5 | 0.9 |
| G6 | 2.0 |
| G7 | 1.7 |
| G8 | 0.5 |
| G9 | 0.3 |
| G10 | 0.3 |
| G11 | 0.2 |
| G12 | 0.2 |
| G13–14 | 5.8 |
| G15 and over | 86.1 |

Thus, the polymer mixture contained 91.9 wt. % of polymers of D.P. greater than 12 and 7.9 wt. % of polymers of from D.P. 2 to 10. The average molecular weight of this polymer mixture, determined by H.P.L.C., was 23,700. This glucose polymer mixture was the subject of clinical and other tests and is referred to below as "the glucose polymer mixture of Example 7."

EXAMPLE 8

23 kg of the glucose polymer mixture described in Example 5 was dissolved in water, the solution having a volume of 37 litres. 32.5 litres of 85% w/w ethanol was added. After allowing two phases to separate by settling over four hours, the high molecular weight lower syrup phase, containing approximately 10% of the polymers, was withdrawn and discarded. To the upper phase was added 40 litres of 85% w/w ethanol, to precipitate a further 53% of the original polymers. This syrup phase (21 litres) was diluted to 46 litres with water and re-precipitated with 75 litres of 85% w/w ethanol to yield 31% of the original glucose polymers. After two further re-precipitations, a yield of 27% of the original. glucose polymers was isolated. The composition of the polymer mixture thus obtained was as follows:

| | Weight % |
|---|---|
| G1 | 0.15 |
| G2 | 0.5 |
| G3 | 0.8 |
| G4 | 0.6 |
| G5 | 0.9 |
| G6 | 2.2 |
| G7 | 1.9 |
| G8 | 0.6 |
| G9 | 0.3 |
| G10 | 9.3 |
| G11 | 0.1 |
| G12 | 0.1 |
| G13–14 | 5.6 |
| G15 and over | 85.8 |

Thus, the polymer mixture contained 91.4 wt. % of polymers of D.P. greater than 12 and 8.25 wt. % of polymers of from D.P. 1 to 10. The average molecular weight of the polymer, mixture, determined by H.P.L.C., was 19,800.

EXAMPLE 9

Clinical tests were carried out by subjecting an adult male to peritoneal dialysis with two compositions. Each composition was a solution of a type conventionally used in peritoneal dialysis, the compositions differing only in the nature of the osmotic agent used. One composition (Solution A) contained 1.36% by weight of dextrose and the other composition 5% by weight of the glucose polymer mixture of Example 7 above. The results of the tests are summarized as follows:

1. The degree of ultrafiltration was comparable for the two solutions. In each case the patient received 2.2 litres of solution. After three hours the solution was withdrawn from the patient and for Solution A the withdrawn volume amounted to 2.375 litres whereas for Solution B it amounted to 2.430 litres.

2. The levels of uric acid, phosphates, creatinine, and urea in the serum and in the dialysate were determined. After a three hour dwell of solution in the peritoneum the ratios of concentration in the dialysate to concentration in the serum were as follows:

| | Solution A | Solution B |
|---|---|---|
| Uric acid | 0.60 | 0.89 |
| Phosphate | 0.68 | 0.91 |
| Creatinine | 0.73 | 0.96 |
| Urea | 0.94 | 1.10 |

It is clear that Solution B gives a more efficient extraction than Solution A. The fact that the concentration of urea is higher in the dialysate than in the serum is remarkable and unexpected. This effect may be due to the formation of inclusion complexes of urea with glucose polymer molecules. It is believed that higher molecular weight glucose polymers have helical structures when in solution and it is therefore possible that they could form such complexes.

3. The initial osmolality of Solution A was 334 mOsm/kg; that of Solution B was 311 mOsm/kg. After three hours the osmolality of the dialysate formed by Solution A was about 80% of the original value, whereas the osmolality of the dialysate formed by Solution R remained the same as the original value.

EXAMPLE 10

Two litres of Solution B of Example 9 were introduced into the peritoneum of an adult non-diabetic male and allowed to remain there for six hours. During that time the serum of the patient was monitored to assess the levels of glucose and of total carbohydrate. The results (in mg/dl) were as follows:

| Time (hrs) | Serum glucose | Serum carbohydrate |
| --- | --- | --- |
| 0 | 79.5 | 140.0 |
| ¼ | 73.5 | 94.0 |
| 2 | 63.5 | 150.0 |
| 4 | 55.2 | 160.0 |
| 6 | 50.5 | 160.0 |

Thus, the dialysis was effected without unduly loading the patient with carbohydrate. It is estimated that with three infusions of Solution B per twenty-four hours the total daily carbohydrate uptake would be about 58 g. By contrast, with a regimen daily involving four infusions of a dialysis solution containing 1.36% dextrose and one infusion of a dialysis solution containing 3.86% dextrose (regimen typical of conventional peritoneal dialysis) the carbohydrate uptake can be expected to be about 136 g.

EXAMPLE 11

Three solutions suitable for use in peritoneal dialysis were prepared, all of similar composition except that as the osmotic agent one solution contained 1.36% dextrose, another contained 3.86% by weight of dextrose and another contained, as the osmotic agent, 5.0% by weight of the glucose polymer mixture of Example 7. The osmolality of each solution was measured with the following results:

| Solution | Osmolality (mOsm/kg) |
| --- | --- |
| 1.36% dextrose | 334.4 |
| 3.86% dextrose | 482.4 |
| 5.0% of glucose polymer mixture of Example 7 | 308.0 |

It is evident that the third of these solutions would in use be less stressful on the peritoneal membrane than either of the other solutions.

EXAMPLE 12

Two solutions suitable for use in peritoneal dialysis were prepared, both of similar composition except that one contained, as the osmotic agent, 5.0% by weight of the glucose polymer mixture of Example 7 above, whereas the other contained, as the osmotic agent, 5.0% by weight of the glucose polymer mixture of Example 5. These solutions were used in peritoneal dialysis on the same patient. The total carbohydrate content was measured for each of the final dialysates after six hours. It was found that the amount of carbohydrate lost from the peritoneum with the first solution was 22.7% and with the second solution 44.9% The carbohydrate load on the patient was therefore considerably lower for the first solution than for the second.

The nature of the carbohydrate load imposed on the patient by these two solutions is of some significance. The glucose polymer mixture used in the first solution contains 7.9% of polymers of D.P. from 2 to 10, whereas the second solution uses a glucose polymer solution containing 61.8% of polymers of from D.P. 1 to 10. When dialysis is carried out with either solution, there occurs diffusion of polymers of all molecular weights across the peritoneal membrane into the blood. In each case, the lower molecular weight polymers permeate the membrane more rapidly than do the higher molecular weight polymers. However, because of the different composition of the glucose polymer mixtures used as osmotic agents, the carbohydrate load imposed by the first solution comprises a lower proportion of lower molecular weight polymers and a higher proportion of higher molecular weight polymers than does the load imposed by the second solution.

It appears that the higher molecular weight polymers are degraded in the blood by plasma amylase to give polymers of lower molecular weight. These polymers, for example maltotrioses, are not very readily metabolized or eliminated. The concentration of such polymers in the first solution is relatively low and they can therefore be removed from the blood by diffusion through the peritoneal membrane much more rapidly than is possible when the second solution is being used for dialysis, since the second solution already contains a high concentration of such polymers. Thus, the first solution may be said to have the capability of removing its own breakdown products from the blood.

This is illustrated by observations made in the course of the comparative tests described above. During the dialysis using the first solution, the glucose levels of the serum and of the dialysate were monitored. Initially, the serum glucose level (expressed in millimoles per litre) was 4.3. During the first hour it fell to 4.0, during the second hour it rose to 4.4, and during the last four hours it gradually fell to 4.2. The glucose level of the dialysate (initially insignificant) rose rapidly during the first hour to 2.1 and then less rapidly over the last five hours to reach 4.4. It will be recognized that the maintenance of a substantially constant glucose level in the blood, accompanied by a continuously rising level of glucose in the dialysate is consistent with a process in which higher molecular weight polymers that have entered the blood from the dialysate being enzymatically hydrolysed to form, inter alia, glucose which is then withdrawn into the dialysate, at least until such time as the concentration of glucose in the dialysate rises to equal that in the blood. A similar process appears to take place in respect of the oligosaccharides, the build-up of which in the blood has caused problems for some patients, i.e. lower molecular weight polymers are formed in the blood by hydrolysis of higher molecular weight polymers and then diffuse into the peritoneum. With regard to this, the serum maltose level of the patient was determined after six hours of dialysis. It was found that when the first solution was used the final serum maltose level was 0.15 g/l whereas for the second solution it was 1.02 g/l.

It may be mentioned that polymers of all molecular weights are able to find their way into the blood by a route other than by diffusion through the peritoneal membrane, possibly by way of the lymphatic system.

The peritoneal dialysis compositions of the present invention are of value not only in the treatment of patients suffering from kidney malfunction but also in the treatment of patients suffering from toxaemia of other origins.

Accordingly, the invention also provides a method of treating a patient suffering from toxaemia caused other than bv kidney malfunction, comprising effecting peritoneal dialysis by introducing into the abdominal cavity of the patient a peritoneal dialysis composition including as an osmotic agent a glucose polymer mixture containing at least 15% by weight, preferably more than 50% by weight, of glucose polymers of D.P. greater than 12.

Such toxaemia may be caused by toxins which arise from internal disorders of the body or are derived from external sources.

Various diseases and disorders give rise to toxaemia which can be treated by peritoneal dialysis using as osmotic agents the glucose polymer mixtures referred to. They include gout, hepatic encephalopathy, amino acid opathies (MSUD), neurological disorders caused by accumulation in the blood of long chain fatty acids, and cases of intractable heart failure in which an excess of water in the blood constitutes the toxin.

Toxaemia caused by toxins from sources external to the body includes cases of poisoning by overdoses of drugs, for example barbiturates, salicylates, lithium, and guinidine, and industrial or agricultural chemicals, for example the herbicide paraquat.

In considering the potential value of treatment of such toxaemia by peritoneal dialysis using, as osmotic agents, the glucose polymer mixtures referred to, it is necessary to take into account the fact that the rate of removal of a chemical from the body into the peritoneal fluid will depend on a number of factors which include:

1. The degree of plasma protein binding of the chemical, because only molecules which are free in the plasma water will be dialysed.

2. The volume of distribution of the chemical, which determines the proportion of the total body burden of the chemical which is in the blood and is therefore irnpediately available for dialysis. If the volume of distribution is high (i.e. the proportion of total chemical in the blood is low) then dialysis for prolonged periods will be needed to effect a significant removal of the chemical.

Furthermore, the value of such treatment is subject to:

(a) whether a significant rate of clearance can be achieved, (b) whether the rate of clearance is substantial when compared with the body's normal rate of clearance (by metabolism or excretion), and (c) whether peritoneal dialysis can be quickly and easily initiated on a patient.

With regard to (c) it appears that in most cases peritoneal dialysis could be intitiated more quickly and easily than haemodialysis or haemoperfusion and probably with less risk of harming the patient. In addition, unlike haemoperfusion, it should be possible to continue with peritoneal dialysis for prolonged periods, so as to avoid rebound of the blood level of the chemical (due to influx from the tissues) that can occur when haemoperfusion has to be stopped because of such problems as loss of platelets.

As mentioned above, any binding of the chemical to plasma proteins would limit the rate of clearance of the chemical to the peritoneum because only unbound chemical is free to equilibrated with that in the dialysis solution. However, in a case where it is possible to reduce the free concentration of the chemical in the dialysis solution to a level below that in the plasma, a better clearance can be achieved. Natural or synthetic complexing agents may be considered for this purpose. For example, the inclusion of human albumin in the dialysis solution may in some cases offer the possibility of effecting improved clearance of some drugs, such as tricyclic anti-depressants which are highly bound to plasma protein.

A discussion of the potential value of peritoneal dialysis for the treatment of paraquat poisoning will serve for illustration of this aspect of the invention. (Paraquat is a trade name for the herbicide 1.1'-dimethyl-4-4'-dipyridium dichloride.)

In the paraquat (PQ) poisoned patient an early and important event is renal failure. The time of onset and degree of renal failure determines how much PQ is retained in the body to allow the slow accumulation of toxic concentrations in the lung. The kidney lesion is reversible but the lung lesion is not and is usually the cause of death unless the patient has taken a massive dose and dies within 2–3 days. A method for removing PQ from the circulation in the interval between onset of renal failure and accumulation of toxic levels in the lung (approximately 12–18 hours in man) would be valuable. This method must be readily instituted (within 1 hour) and must be capable of being maintained for long periods (3–4 days) until renal function begins to return and the body burden of PQ has been largely eliminated.

Peritoneal dialysis with the glucose polymer mixtures referred to above represents an attractive and better alternative to haemodialysis or haemoperfusion for the removal of PQ. The purpose of the study described below was to determine whether a solution of the specified glucose polymers in the peritoneum of a dog extracts PQ from the circulation.

EXPERIMENTAL PROCEDURE

A 28.5 kg greyhound dog was anaesthetized with pentobarbital. A venous cannula was inserted into one foreleg vein for collection of blood samples and into the other for administration of PQ. A bladder catheter was inserted for collection of urine. An intravenous dose of 20 mg,/kg (570 mg and 116 ug of $^{14}$C-PQ—51.5 uCi) of paraquat was administered over a 5 minute period. Urine samples were collected every hour, volume was recorded and aliquots were taken for measurement of radioactivity. Blood samples were taken every 30 minutes, plasma was separated and counted. Two hours after the administration of the paraquat 33 ml/kg (1180 ml) of a peritoneal dialysis solution (of conventional composition except that instead of dextrose the solution contained, as the osmotic agent, 10% by weight of the mixture of glucose polymers of Example 5 was introduced into the peritoneum through a catheter. Samples of the dialysis fluid were taken at intervals for two hours. Two hours after the introduction of the peritoneal dialysis fluid, it was removed and the experiment was terminated.

RESULTS

The experiment was completed according to the protocol. However, the intravenous dose of paraquat did not induce renal failure within 2 hours as was expected. The renal clearance of paraquat did not decline (Table 1). A larger dose with a longer time period would evidently be needed to cause renal failure. Nevertheless, this study clearly shows that paraquat readily passes from the blood into the dialysis fluid in the peritoneum (Table 2). The rate of rise of the concentration of paraquat in the peritoneum was rapid at first so that half equilibration with the plasma concentration was achieved in 40 minutes. A similar result was obtained in a further study with another dog. If we assume that half-equilibration with plasma concentration is achieved in 40 minutes in a poisoned patient with renal failure and that a total of 4 litres of fluid is introduced into the peritoneum then by changing the fluid at intervals of 40 minutes to 1 hour a clearance of paraquat of 2000/40 ml per min or 50 m./min could be achieved. This is far greater than renal clearance in the poisoned patent and is comparable to values obtained with haemodialysis or haemoperfusion (60–100 ml/min).

TABLE 1

RENAL CLEARANCE OF PARAQUAT

| Time (h) | Clearance (ml/min) |
|---|---|
| 1.5 | 64.3 |
| 2.5 | 48.4 |
| 3.5 | 56.0 |

TABLE 2

PERITONEAL DIALYSIS OF PARAQUAT
The appearance of paraquat in the dialysate

| Time (min) | Paraquat (ug/ml) |
|---|---|
| 0 | 0 |
| 15 | 2.89 |
| 30 | 3.67 |
| 47 | 4.72 |
| 60 | 5.73 |
| 87 | 6.06 |
| 120 | 6.40* |

*(Plasma paraquat 8.9 ug/ml)

In the following examples, clinical studies were carried out which compared low molecular weight glucose polymers having a D.P. between 2 and 7 with high molecular weight glucose polymers having a D.P. of greater than 12 for use in peritoneal dialysis solutions. The background and protocol for such studies are set forth below:

INTRODUCTION

Since the introduction of continuous ambulatory peritoneal dialysis (CAPD) in 1976, the number of patients on long-term peritoneal dialysis has steadily increased throughout the world. The rapid expansion of this treatment in the UK is probably due to:

1. The relative cost of the treatment.
2. The basic philosophy of training patients for self-care at home.

CAPD is a relatively simple procedure for trained patients to perform at home since all it entails is exchanging 2 litres of PD. Fluid in and out of the peritoneal cavity three to four times a day. The chemical composition of the dialysis fluid, particularly the osmotic agent, is vital in determining the efficiency of the system. The osmotic agent raises the osmotic pressure of the solution above that of plasma and permits removal of water (ultra-filtration) and enhances diffusion of waste products from the body. The most widely used osmotic agent is glucose. Glucose is safe, effective, economical and rapidly metabolised. However, major disadvantages of long term continuous use of glucose in CAPD are primarily related to rapid absorption through the peritoneum resulting in:

1. Ultrafiltration of short duration.
2. Metabolic complications such as hyperglycaemia, hyperinsulinaemia, hyperlipidaemia and obesity.

In addition, hyperosmolar solutions may damage the peritoneal membrane and limit the effective lifetime of this treatment. These disadvantages have led to a search for alternative osmotic agents.

An ideal osmotic agent should have the following characteristics:

1. Good ultrafiltration and solute clearances.
2. Minimal absorption of the osmotic agent from the peritoneal cavity so as to maintain osmolality.
3. Rapidly metabolised.
4. Non-toxic to the peritoneum.

AIMS

The purpose of the clinical studies was to compare the performance of various preparations of starch-derived glucose polymers (GP) with the performance of glucose (G), as osmotic agents in standard CAPD Ringer-lactate solutions. Parameters to be monitored include:

1. Ultrafiltration rate.
2. The rate of change of dialysate osmolality.
3. Solute eguilibriation and clearance.
4. Carbohydrate absorption from the peritoneal cavity.
5. The metabolism of absorbed GP.
6. Tolerance of the solution by the patients.

PHASE 1 CLINICAL STUDY

THE POLYMER PROFILE

Solutions containing GP with weight average molecular weight MW 7,000 (GP1) were used in this phase of the study. Chromatographic analysis of the GP1 molecular weight profile showed a bimodal distribution with a "low molecular weight fraction" (54.2%—containing 2 to 7 G units, average 5–6 G units) and a "high molecular weight fraction" (36.9% containing>12 G units).* The glucose polymer test solution had the following composition:

| COMPOSITION | POLYMER GP1 | |
|---|---|---|
| % W/V Polymer | 5 | 10 |
| Average Molecular Weight | 7,000 | 7,000 |
| Lactate mmol/l | 45 | 45 |
| Sodium meq/l | 140 | 131 |
| Calcium meq/l | 3.6 | 3.6 |
| Magnesium meq/l | 1.5 | 1.5 |
| Chloride meq/l | 91 | 91 |

The composition of the polymer mixture is shown below:

| | GP1* |
|---|---|
| G1 | 1.0 |
| G2 | 4.9 |
| G3 | 9.0 |
| G4 | 6.4 |
| G5 | 7.9 |
| G6 | 15.3 |
| G7 | 11.6 |

-continued

|  | GP1* |
|---|---|
| G8 | 3.2 |
| G9 | ⎫ |
| G10 | ⎬ 4.7 |
| G11 | |
| G12 | ⎭ |
| G13–14 | 6.7 |
| G15 and over | 30.2 |
| Estimated average D.P. = 10–15 | 100.0% |

The analysis of the GP1 shows the following contents of the named fractions:

|  | GP1* |
|---|---|
| Glucose, % | 1.0 |
| D.P. greater than 12 | 36.9 |
| D.P. 2–7 | 54.2 |

STUDY AND DESIGN

An open crossover study to compare GP1 solutions, 5% and 10%, with commercially available glucose (G) solutions of 1.36 wt. % and 3.86 wt. % respectively in a single dwell of six hours. The commercial glucose test solutions had the following composition:

| COMPOSITION | G | G |
|---|---|---|
| Glucose, % | 1.36 | 3.86 |
| % W/V (G) Polymer | 0 | 0 |
| Average Molecular Weight | — | — |
| Lactate mmol/l | 35 | 35 |
| Sodium meq/l | 132 | 132 |
| Calcium meq/l | 3.5 | 3.5 |
| Magnesium meq/l | 1.5 | 1.5 |
| Chloride meq/l | 102 | 102 |

SUBJECT AND METHODS

Studies were carried out on 5 non-diabetic patients (3 male; 2 female) aged 22–53 years who had been stable on CAPD for a mean period of 17.1 months (range 3.5–32 months). They were stabilised on 4 exchanges per day and had been free of peritonitis for at least three months prior to the study.

Each patient underwent 4 separate six hour exchanges, in a random order using 2 litres dialysis fluid containing either 1.36% or 3.86% G or GP1 5% or 10%. The 1.36% G and 5% GP1 are generally described as "isotonic" type solutions, whereas 3.86% G and 10% GP1 as "hypertonic" type solutions.

After an overnight fast (10–12 hours), subjects were admitted to a hospital metabolic procedure room, dialysate was drained and 2 litres of fresh fluid were infused by gravity over 10 minutes. Blood and dialysate samples were taken simultaneously prior to dialysis and at 0, 15, 30, 60, 90, 120, 180, 240, 360 minutes; time zero being the end of infusion. At the end of 6 hour dwell, the fluid was drained and volume recorded. Normal dialysis schedule resumed except after the use of GP1 when the dialysis was discontinued for 24 hours and additional blood samples were taken at 3, 14 and 24 hours. Each study was separated by a 48–72 hours interval,

ASSAY METHODS

The serum and dialysate biochemistry was determined by Vickers M300 multichannel autoanalyser, glucose by glucose oxidase method, osmolality by the freezing point deperssion method and GP molecular weight distribution by gel-permeation chromatography, on a Bio-gel $P_2$ column, using a modified Jelco 6AH automatic carbohydrate analyser with an orcinol-sulphuric acid detection system.

Statistical analysis was by student's paired t tests. All values are expressed as mean±standard error of mean (SEM).

RESULTS i ULTRAFILTRATION

Net ultrafiltration by drainage volume was significantly greater with GP1 solution than G for both "isotonic" (580±30 versus 235±57 ml) and "hypertonic (1300±80 versus 935±78 ml) fluids.

ii. OSMOLALITY

The initial dialysate osmolality of GP1 solutions was lower compared to that of G solutions for both "isotonic" (323±0.86 versus 334±1.5 mos/kg. P 0.05) and "hypertonic" (378±3.2 versus 482±1.6; P 0.05). FIG. 1 attached hereto shows the rate of fall in dialysate osmolality expressed as a percentage of initial osmolality was considerably slower for GP1 solution compared to G solution, for both strengths of solutions throughout the dwell period.

iii. SOLUTE TRANSPORT a) Eguilibriation: urea, creatinine, uric acid and phosphate all equilibrated faster with GP1 solution compared to G solution; a significant difference occurred as early as 60 minutes after the onset of dialysis and progressively increased throughout the cycle so that at 6 hours 14.8%, 19% and 21% greater eguilibriation was achieved for creatinine, uric acid and phosphate respectively.

b) Average Clearances: Average clearances of all solutes was significantly greater with GP1 solutions (Tables I and II).

c) Dialysate protein loss: Loss of total protein and albumin in dialysate over 6 hour dwell was greater with GP1 compared with G solutions at both concentrations.

TABLE I

AVERAGE CLEARANCE (ml/min) G: 1.36% v's GP1: 5%

| Solutes | G:1.36% | GP1:5% | % Increase |
|---|---|---|---|
| Urea | 6.7 ± .14 | 7.9 ± .14 | 18 |
| Creatinine | 5.3 ± .27 | 7.2 ± .09 | 36 |
| Uric acid | 4.7 ± .27 | 6.7 ± .18 | 46 |
| Phosphate | 4.7 ± .36 | 6.9 ± .18 | 47 |

TABLE II

AVERAGE CLEARANCE (ml/min) G:3.86% v's GP1:10%

| Solutes | G:3.86% | GP1:10% | % Increase |
|---|---|---|---|
| Urea | 8.7 ± .23 | 10.0 ± .32 | 15 |
| Creatinine | 6.7 ± .18 | 9.2 ± .32 | 37 |
| Uric acid | 5.7 ± .27 | 8.5 ± .36 | 49 |
| Phosphate | 5.7 ± .27 | 8.8 ± .41 | 54 | iv. CARBOHYDRATE ABSORPTION FROM THE PERITONEAL CAVITY
a) Total Carbohydrate Absorption At the end of a 6 hour dwell the percentage of the initial carbohydrate load absorbed from the peritoneal cavity was lower for GP1 (53.4%–58.4%) compared to G (66.0%–68.8%) solutions. However, the total amount of carbohydrate absorbed from "isotonic" and "hypertonic" GP1 solutions was 4 and 2.1 times greater than G solution respectively. Hence, complete metabolism of absorbed GP1 fractions would lead to greater calorific load than G solutions.

b) Glucose Polymer Fraction GP1

The loss of individual polymer fractions from the peritoneal cavity varied considerably during the 6 hour dwell.

Fraction 2–3 G units: 60–70% of initial load absorbed
5–9 G units: 75% of initial load absorbed
12 G units: 24–35% of initial load absorbed Fraction G5–9, although larger than G2–3, showed maximal absorption. This discrepancy appeared to be due to rapid degradation of G5–9 fractions by circulating serum amylase to G2–3 which then diffuses back into the peritoneal cavity.

V. METABOLISM
a) Serum Glucose+Insulin

The rise in blood glucose (6.7±0.3 mmol/l) and insulin noted with "hypertonic" G dialysate (3.86%) was not found using GP1 solution.

b) Serum Polymer Fractions

FIG. 2 attached hereto shows the serum profile at the end of a 6 hour dwell. The fractions showing Predominant elevation are maltose (G2) and maltotriose (G3), accounting for up to 77% of total polymer rise. The peak serum maltose level was 1148±262 mg/l, 32 times greater than pre-dialysis level, with 5% GP solution and it approximately doubled with 10% solution.

FIG. 3 attached hereto shows 80% of the maximum rise of maltose occurred within 2 hours of dialysis and the serum clearance of maltose and maltotriose was slow, up to 90% of maltose and 55–75% of maltotriose still remained 24 hours after stopping the dialysis.

ADVERSE EFFECTS

Three patients experienced "cramp like" abdominal and right shoulder tip pain during infusion of dialysate which resolved completely 20 minutes after the infusion. No other adverse effects were noted in any patients throughout the exchange.

CONCLUSIONS

This study demonstrates the safety and efficacy of glucose polymer GP1 as an osmotic agent. The use of bimodal formulation of GP1 (MW 7,000) is limited by rapid serum rise and slow metabolism of maltose.

PHASE 2 CLINICAL STUDY

The phase 1 study demonstrated superior ultrafiltration and solute clearances for glucose polymer GP1. However, the value of this formulation (bimodal) is limited by rapid accumulation of circulating maltose which is metabolised slowly. Two major sources of circulating maltose appear to be the hydrolysis of rapidly absorbed "low MW fraction" and maltose already present in the dialysate solutions. A maltose free dialysate solution containing "high MW fraction" may greatly reduce the serum maltose load. However, it was difficult to predict the relative contribution of the "high MW fraction" to total ultrafiltration and solute clearances observed in the Phase 1 study. The bimodal polymer preparation was therefore fractionated into:

1) Fraction A="high MW fraction" of MW 20,000 (GPA)
2) Fraction B="low MW fraction" of MW 1,000 (GPB)

These two fractions were used in studies as described for Phase 1 and the test solutions had the following composition:

| COMPOSITION | POLYMER | |
|---|---|---|
| | GPA | GPB |
| % W/V Polymer | 5 | 5 |
| Approximate Average Molecular Weight | 20,000 | 1,000 |
| Lactate mmol/l | 45 | 45 |
| Sodium meq/l | 131 | 131 |
| Calcium meq/l | 3.6 | 3.6 |
| Maqnesium meq/l | 1.5 | 1.5 |
| Chloride meq/l | 91 | 91 |

The composition of the polymer mixture is shown below:

| | GPA % | GPB % |
|---|---|---|
| G1 | 0.1 | 3.0 |
| G2 | 0.5 | 12.8 |
| G3 | 0.8 | 18.3 |
| G4 | 0.6 | 10.5 |
| G5 | 1.0 | 11.6 |
| G6 | 2.2 | 21.3 |
| G7 | 1.9 | 13.5 |
| G8 | 0.6 | 2.6 |
| G9 | 0.3 | 1.1 |
| G10 | 0.3 | 0.9 |
| G11 | 0.0 | |
| G12 | 0.0 | |
| G13–14 | 5.6 | 4.3 |
| G15 and over | 85.8 | |
| Total | 99.7 | 99.9 |

It can be seen that the glucose polymers had the following composition

| | GPA % | GPB % |
|---|---|---|
| Glucose, % | 0.1 | 3. |
| D.P. greater than 12 | 91.4 | <4.3 |
| D.P. 2–7 | 7.0 | 88.0 |
| Average D.P. | >12 | 2–7 |

FRACTION B (GPB 5%)

The result with low molecular weight Fraction CPB may be briefly summarized as follows: Ultrafiltration and solute clearances were greater with GPB 5% solution than with 1.36% G. However, carbohydrate absorption as a % of initial load was the same with both GPB and G solutions whilst serum maltose rose to 30 times the pre-dialysis level following GPB dialysis.

Glucose polymer GPR corresponds to the low molecular weight glucose polymers (average D.P. of less than 10) described in prior art European Patent Application 0076355 to Ramsay and PCT Application WO83/00087 to Alexander et al. The carbohydrate absorption into the serum from the peritoneum using the prior art solutions was so great that it proved unacceptable in clinical practice. This is further confirmed by the publication "Frontiers in Peritoneal Dialysis" by James F. Winchester, M. D., February 1986.

FRACTION A (GPA 5%)

GPA, like GPB, gave significantly greater solute clearance value than 1.36% G but the % absorption of carbohydrate was considerably lower for GPA (35%) as compared to either 1.36% G or GPB 5% (60%). Serum maltose levels after 6 hours of dialysis with GPA were very much lower than seen with GPB and were only 30% of those seen with the bimodal preparation used in Phase 1. Thus the "high MW fraction" was an effective and acceptable osmotic agent with reduced carbohydrate absorption.

In the study with GPA, two of the three patients developed severe abdominal pain 4–5 hours after the infusion of the polymer solution, and the drained dialysate was cloudy and contained fibrin. The symptoms resolved completely after 3×2 litre lavage with 1.36% G solution. The reaction in these patients was suggestive of an acute chemical peritonitis. Studies conducted in rats strongly suggested that it was a pyrogen (endotoxin) mediated effect.

Although interpretation of the results in these studies is complicated by the "peritonitis" in two patients, a number of conclusions can be made.

1) Fraction GPB is not responsible for all the ultrafiltration seen with the bimodal preparation in the Phase 1 study.
2) Fraction GPA (5%) solution, despite being almost isosmolar to uraemic serum, produced ultrafiltration similar to 1.36% G. In addition carbohydrate absorption was greatly reduced and dialysate osmolality maintained for the 6 hour dwell time. Serum maltose levels were reduced compared with bimodal preparation.

These results suggested that a finely fractionated preparation with a MW of 20,000 essentially free of maltose or maltotriose might prove to be an effective osmotic agent. Accordingly, a fractionated glucose polymer with a molecular weight of 20,000, identified as GP2, was used in Phases 3 and 4 of the clinical study.

PHASE 3 CLINICAL STUDY

THE POLYMER PROFILE

A "high MW fraction" (MW 20,000; GP2) isolated by fractionation of bimodal dextrin, was rendered free of pyrogens (endotoxins) with charcoal. The chromatographic analysis showed that the polymer was essentially free of maltose (G2) and maltotriose (G3) and 95.4% of the polymer comprised a fraction of >2 G, units (FIG. 4 attached hereto); 80% of the MW distribution of this product was between 5,000–50,000 daltons. The test solution had the following composition:

| POLYMER | GP2 |
| --- | --- |
| % W/V Polymer | 5 |
| Average Molecular Weight | 20,000 |
| Lactate mmol/l | 45 |
| Sodium meq/l | 140 |
| Calcium meq/l | 3.6 |
| Magnesium meq/l | 1.5 |

-continued

| POLYMER | GP2 |
| --- | --- |
| Chloride meq/l | 100 |

The composition of the polymer mixture is shown below:

| | GP2 |
| --- | --- |
| G1 | 0.4 |
| G2 | 0.0 |
| G3 | 0.1 |
| G4 | 0.2 |
| G5 | 0.4 |
| G6 | 0.8 |
| G7 | 0.8 |
| G8 | 0.4 |
| G9 | |
| G10 | ~1.6 |
| G11 | |
| G12 | |
| G13–14 | 8.8 |
| G15 and over | 86.6 |
| Total | 100.1% |

It can be seen that GP2 had the following composition:

| | GP2 |
| --- | --- |
| Glucose, % | 0.4 |
| D.P. greater than 12 | 95.4 |
| D.P. 2–7 | 2.3% |
| Average D.P. greater than 15 | |

After 6 hour exchange with 5% GP2 the serum maltose level reached 214 mg/l, which is a 6 fold increase when compared to predialysis values. However, this value is 80% lower than previously observed (1068 mg/l) following dialysis with the bimodal preparation, 5% GP1 (MW 7,000), solution for similar duration (FIG. 6 attached hereto).

Although the clearance of serum maltose appears to be extremely slow in the absence of dialysis (FIG. 7 attached hereto), adequate peritoneal clearance can be achieved during peritoneal dialysis.

Adverse Effects

Only one patient experienced transient infusion associated "cramp like" abdominal pain lasting 20 minutes.

CONCLUSIONS

A glucose polymer of high MW (20,000 daltons) is a safe and effective osmotic agent for CAPD. Its unique properties (sustained ultrafiltration and enhanced solute clearance achieved with a low dialysate osmolality and potentially low calorie load) point to considerable clinical advantages.

PHASE 4 CLINICAL STUDY—MULTIPLE EXCHANGES

The purpose of this was to evaluate:

i. Sustained ultrafiltration characteristics of 5% GP2 by varying the length of dwell time.
ii. To monitor the change in dialysate osmolality.
iii. To measure protein loss into the dialysate.
iv. To monitor the accumulation and metabolism of serum maltose.

SUBJECT AND METHODS

Four of the 5 patients from the Phase 3 study underwent 3 consecutive 2 litre exchanges with 5% GP2 (MW 20,000) solutions over a period of 26 hours, the GP2 being the same polymer mixture as that used in Phase 3. The duration of first, second and third exchange were 8 hours, 6 hours and 12 hours respectively. Each patient underwent a similar study using 2 litre of 1.36% glucose solution.

RESULTS

Ultrafiltration was greater with 5% GP2 than 1.36% G for all three exchange periods (Table IV) and was particularly impressive for the 12 hour dwell.

TABLE IV

Ultrafiltration (ml) with GP2 and G over 26 hrs (n = 4)

| Preparation | 6 hrs | 8 hrs | 12 hrs |
|---|---|---|---|
| G: 1.36% | +100 ± 21 | −61 ± 48 | −62 ± 83 |
| GP2: 5% | +225 ± 69 | −225 ± 94 | +531 ± 28 |

TABLE V

Protein loss (g) with GP2 and G over 26 hours (n = 4)

| Preparation | 6 hrs | 8 hrs | 12 hrs |
|---|---|---|---|
| G: 1.36% | 1.86 ± 0.35 | 3.30 ± 0.76 | 4.80 ± 0.71 |
| GP2: 5% | 1.81 ± 0.29 | 3.10 ± 0.40 | 3.49 ± 0.16 |

Solute Transport

Solute equilibrium ratios (D/P ratio) were the same for the two solutions beyond 6 hour dwell time. However, solute clearance were higher with 5% GP2 because of superior ultrafiltration.

CONCLUSION

This study clearly demonstrates that sustained ultrafiltration beyond 12 hours is possible with high MW glucose polymers (20,000).

PHASE 5 CLINICAL STUDY

The purpose of this study (open crossover) was to compare a standard dialysis schedule consisting of four, two litre glucose (G) exchanges per day (three of 1.36 wt. % and one of 3.86 wt. % overnight) in which the hypertonic glucose exchange of 3.86 wt. % is replaced by 5% GP2 (GP2 being the same polymer mixture as that used in Phases 3 and 4) solution for a duration of 5 to 7 days. The parameters to be monitored were as follows:

i. Total ultrafiltration per day
ii. Solute transport
iii. Carbohydrate absorption and caloric load
iv. Accumulation and metabolism of maltose+HMW
v. Toxicity.

SUBJECTS AND METHODS

Five non-diabetic patients were selected for the study, four males and one female. All of the patients were well established on CAPD with no catheter or drainage problems. All of the patients were free from peritonitis for at least 3 months. The study was conducted in two stages; the first stage being a standard glucose exchange conducted at home where each patient performed a total of four exchanges per day with two litres of peritoneal dialysis solution containing glucose (G). The standard glucose solutions had the composition described in Phase 1. The composition of the GP2 test solution is set forth below. The concentration and time of each exchange was as follows:

| POLYMER | GP2 |
|---|---|
| % W/V Polymer | 5 |
| Average Molecular Weight | 20,000 |
| Lactate mmol/l | 45 |
| Sodium meg/l | 130 |
| Calcium meg/l | 1.81 |
| Chloride meg/l | 105 |
| Magnesium meg/l | 1.5 |
| Dialysate Osmolality (MOSM/L) | 265 |

STAGE 1:
1. 08.00 hr.: 1.36% G (4 hr. dwell)
2. 12.00 hr.: 1.36% G (4 hr. dwell)
3. 16.00 hr.: 1.36% G (4 hr. dwell)
4. 20.00 hr.: 3.86% G (12 hr. dwell)

DAILY PROCEDURES a) Record daily body weight at 8:00 a.m. (with abdomen empty)
b) Record the weight of each bag, before and after exchange
c) Dialysate samples
  20 ml of dialysate fluid will be collected from the drained bag, after each exchange, for estimating urea, creatinine, electrolytes, glucose, uric acid, phosphate, total protein, albumin.
d) Blood samples
  12 ml of blood will he collected (plain bottle) from each patient before and at the end of the study (7th day), for above parameters.
e) Urine
  A single 24 hour urine collection will be analyzed from each patient for estimating residual renal function.

STAGE 2: "Modified Regime"

5% GLUCOSE POLYMER SOLUTION substituted for an overnight 3.86% G exchange.

PARAMETERS TO BE MONITORED

1. Record daily body weight (at 8:00 a.m., with abdomen empty of P.D. Fluid).
2. Record daily temperature—at 8:00 a.m.
3. Blood pressure and pulse should he recorded at 8:00 a.m. and 4:00 p.m.

During GP Exchange a) BP+pulse should be recorded at 15, 30 and 60 minutes after completion of infusion. No further BP monitoring is necessary if patient experiences no side effects.
b) Adverse effects
  i) abdominal pain/discomfort during the infusion or dwell period
  ii) nausea or vomiting
  iii) cloudy fluid—send for C+S differential WCC—poly+esinophils

DIALYSATE SAMPLES 20 ml of dialysate will be withdrawn at the end of each exchange for estimating urea, creatinine, phosphate, uric acid, total protein, albumin, glucose and GP fractions.

BLOOD SAMPLES 12 ml of venous blood (plain bottle—clotted sample) will be withdrawn daily from each patient, before and after each GP exchange. Serum will be separated from all samples and frozen immediately until analysis.

All samples will be analyzed for GP.

Only alternate day samples will be analyzed for U+E, amylase and glucose.

RESULTS

Ultrafiltration

The 5% GP2 solution was capable of producing sustained ultrafiltration (UF) over a period of 12 hour dwell averaging 156 ml. in 5 CAPD) patients (Table 1), even though the total osmalality of the dialysate (276+1.1 mOsm/kg) was considerably lower than uraemic serum (300+3.0 mOsm/kg).

TABLE 1

NET ULTRAFILTRATION ml: (MEAN + SEM) OVER 7 DAYS

| Patients | G: 3.86% | GP2: 5% |
|---|---|---|
| 1 | 886 ± 46 | 300 ± 19 |
| 2 | 1021 ± 38 | 186 ± 14 |
| 3 | 571 ± 125 | 100 ± 42 |
| 4 | 886 ± 40 | 64 ± 24 |
| 5 | 886 ± 34 | 129 ± 30 |
| AVERAGE | 850 | 156 |

SOLUTE TRANSPORT

The transperitoneal transport of solutes expressed as D/P ratio indicates that a majority of small MW solutes, except phosphate, are fully equilibrated at the end of 12 hour exchanges with both G and GP2 solutions (Table 2). Thus, although average clearances of most solutes are expected to he higher with 3.86% G compared to 5% GP solutions in the present study, it would not be the case if the ultrafiltration of both solutions were similar. One exception to this rule is the clearance of phosphate, due to fundamental differences in the equilibration between the solutions. The GP2 solution is, therefore, particularly effective in removing phosphate compared to glucose during long dwell exchanges, even when the ultrafiltration rates are similar.

TABLE 2

D/P PATIO: 12 HR. EXCHANGE (n:35) in 5 PATIENTS MEAN + SEM D/P RATIO %

| | G: 3.86% | GP2: 3.86% |
|---|---|---|
| Urea | 88.5 ± 2.9 | 105 ± 1.0 |
| Creatinine | 90.9 ± 2.2 | 92.4 ± 1.2 |
| Uric Acid | 89.6 ± 2.7 | 98.5 ± 2.2 |
| Phosphate | 76.0 ± 2.3 | 94.7 ± 2.0 |

PROTEIN LOSSES

The loss of protein in the dialysate is on the whole greater with 5% GP compared to 3.86% G solution (Table 3). One possible explanation for this observation may be related to large differences in the initial osmolality of the solutions.

TABLE 3

PROTEIN LOSS PER 12 HR. DWELL (MEAN + SEM) OVER 7 DAYS

| | G: 3.86% | GP: 5% |
|---|---|---|
| a) Conc g/l | | |
| 1 | 1.017 ± 0.348 | 1.466 ± 0.637 |
| 2 | 0.353 ± 0.118 | 0.961 ± 0.094 |
| 3 | 0.521 ± 0.188 | 2.286 ± 0.756 |
| 4 | 0.808 ± 0.064 | 3.167 ± 0.408 |
| 5 | — | — |
| b) Total per exchange (gms) | | |
| 1 | 3.146 ± 1.081 | 3.769 ± 1.747 |
| 2 | 1.145 ± 0.421 | 2.296 ± 0.247 |
| 3 | 1.393 ± 0.345 | 5.221 ± 1.672 |
| 4 | — | — |

CARBOHYDRATE ABSORPTION

As shown in Table 4 below, the mean carbohydrate abosorption associated with 5% GP2 solution (17.2 gm) was substantially lower than 3.86% G (66.8 gm) at the end of 12 hour exchanges representing 17.3% and 81.2% of the initial carbohydrate load, respectively. Furthermore, when compared with previous studies, the total GP absorbed is:

Even lower than glucose absorption (24.9 gm) observed with overnight 1.36 G exchanges in PHASE 4 Study.

ii Virtually identical to total GP absorbed during 6 hr exchanges in PHASE 3 Study (17.7+3.2 gm).

It follows, therefore, that complete metabolizing GP2 absorbed in this study would lead to almost four fold reduction in calories load compared to 3.96% G and 30% lower than 1.36% G overnight changes.

TABLE 4

CARBOHYDRATE ABSORPTION PER 12 DWELL (MEAN + SEM) OVER 7 DAYS

| | G: 3.86% | | GP2: 5% | |
|---|---|---|---|---|
| PATIENTS | gm | % | gm | % |
| 1 | 66.5 ± 1.7 | 78.5 ± 2.0 | 15.3 ± 2.9 | 15.2 ± 2.8 |
| 2 | 61.3 ± 1.0 | 72.4 ± 1.0 | 33.6 ± 2.0 | 23.4 ± 2.0 |
| 3 | 77.1 ± 1.7 | 91.0 ± 2.0 | 15.1 ± 1.2 | 15.0 ± 1.1 |
| 4 | 69.1 ± 0.8 | 82.2 ± 1.0 | 16.5 ± 2.1 | 16.4 ± 2.1 |
| 5 | 59.5 ± 1.0 | 82.0 ± 1.3 | 15.7 ± 2.7 | 15.6 ± 2.7 |
| AVERAGE | 66.8 | 81.2 | 17.2 | 17.3 |

SERUM GP FRACTIONS AND METABOLISM

The measurement of circulating GP2 fraction over 7 days demonstrates that steady state levels are achieved from small molecular weight fractions such as maltose (G2 0.388+0.049 g/l) maltotriose (G3 0.362+0.067 g/l) and IMW.

ADVERSE EFFECTS

It is most important to emphasize that none, of the patients encountered any adverse effect during a period of 7 day study. All patients were active and ambulant throughout the study.

What is claimed is:

1. An aqueous peritoneal dialysis composition sterile and free from pyrogens which is used for introduction into the abdominal cavity for removal of water and waste products by dialysis across the peritoneal membrane comprising a water soluble glucose polymer mixture derived from the hydrolysis of starch containing at least 36.7% by weight of glucose polymers having a degree of polymerization (D.P.)

of more than 12 glucose units, said glucose polymer mixture being present in the peritoneal dialysis composition as an osmotic agent and said peritoneal dialysis composition having an osmolality of about 265 to 378 mOsm/kg.

2. An agueous peritoneal dialysis composition which is used for introduction into the abdominal cavity for removal of water and waste products by dialysis across the peritoneal membrane comprising a water soluble glucose polymer mixture having an average molecular weight of from 15,000 to 25,000 derived from the hydrolysis of starch containing at least 36.7% by weight of glucose polymers having a degree of polymerization (D.P.) of more than 12 glucose units, said glucose polymer mixture being present in the peritoneal dialysis composition as an osmotic agent.

3. The composition of claim 1 or 2 wherein the average molecular weight of the glucose polymer mixture is from 18,000 to 22,000.

4. The composition of claim 1, 2 or 3 wherein the glucose polymer mixture contains more than 50% by weight of glucose polymers having a degree of polymerization (D.P.) of more than 12 glucose units.

5. The composition of claim 1, 2 or 3 wherein the glucose polymer mixture contains from 50 to 90% by weight of glucose polymers having a degree of polymerization (D.P.) of more than 12 glucose units.

6. The composition of claim 1, 2 or 3 wherein the glucose polymer mixture contains from 75 to 100% by weight of glucose polymers having a degree of polymerization (D.P.) of more than 12 glucose units.

7. The composition of claim 1, 2 or 3 wherein the glucose polymer mixture contains from 90 to 100% by weight of glucose polymers having a degree of polymerization (D.P.) of more than 12 glucose units.

8. The composition of claim 1, 2 or 3 wherein the agueous peritoneal dialysis composition contains from 2 to 10% w/v of said glucose polymer mixture.

9. The composition of claim 1, 2 or 3 wherein the agueous peritoneal dialysis composition contains from 2 to 4% of w/v of said glucose polymer mixture.

10. The composition of claim 1, 2 or 3 wherein the glucose polymer mixture contains less than 3% by weight of glucose.

11. The composition of claim 1, 2 or 3 wherein the aqueous peritoneal dialysis composition contains from 2 to 15% w/v of said glucose polymer mixture.

12. The composition of claim 1, 2 or 3 wherein the aqueous peritoneal dialysis composition contains from 2 to 5% w/v of said glucose polymer mixture.

13. The composition of claim 1, 2 or 3 wherein the starch contains not more than 5% of 1,6-linkages.

14. The composition of claim 1, 2 or 3 further comprising 116 to 145 mEg/liter of sodium, 0 to 6 mEg/liter of calcium, 90 to 144 mEg/liter of chloride and 1 to 2 of mEg/liter of magnesium.

15. The composition of claim 1, 2 or 3 containing from 0.5 to 25 g/liter of amino acid salts or protein hydrolyzates.

16. A water soluble glucose polymer mixture having an average molecular weight of from 15,000 to 25,000 derived from the hydrolysis of starch and containing at least 36.7% of glucose polymers having a degree of polymerization (D.P.) of more than 12 glucose units.

17. The composition of claim 16 wherein the average molecular weight of the glucose polymer mixture is from 18,000 to 22,000.

18. The composition of claim 16 wherein the glucose polymer mixture contains more than 50% by weight of glucose polymers having a degree of polymerization (D.P.) of more than 12 glucose units.

19. The composition of claim 16 wherein the glucose polymer mixture contains from 50 to 90% by weight of glucose polymers having a degree of polymerization (D.P.) of more than 12 glucose units.

20. The composition of claim 16 wherein the glucose polymer mixture contains from 75 to 100% by weight of glucose polymers having a degree of polymerization (D.P.) of more than 12 glucose units.

21. The composition of claim 16 wherein the glucose polymer mixture contains from 90 to 100% by weight of glucose polymers having a degree of polymerization (D.P.) of more than 12 glucose units.

22. The composition of claim 16 wherein the starch contains not more than 5% of 1,6-linkages.

* * * * *